United States Patent [19]

Uehara et al.

[11] Patent Number: 5,714,492
[45] Date of Patent: Feb. 3, 1998

[54] SUBSTITUTED AMINOQUINAZOLINONE (THIONE) DERIVATIVES OR SALTS THEREOF, INTERMEDIATES THEREOF, AND PEST CONTROLLERS AND A METHOD FOR USING THE SAME

[75] Inventors: Masahiro Uehara, Sakai; Toshiaki Shimizu, Kawachinagano; Shinsuke Fujioka, Kawachinagano; Masayuki Kimura, Kawachinagano; Kenji Tsubata, Kawachinagano, all of Japan

[73] Assignee: Nihon Nohyaku Co., Ltd., Tokyo, Japan

[21] Appl. No.: 623,192

[22] Filed: Mar. 28, 1996

[30] Foreign Application Priority Data

Mar. 31, 1995 [JP] Japan ................................. 7-099879

[51] Int. Cl.$^6$ ...................... C07D 239/80; A61K 31/505
[52] U.S. Cl. ...................... 514/259; 514/267; 544/284; 544/286; 544/250
[58] Field of Search ........................ 544/284, 286, 544/250; 514/259, 267

[56] References Cited

U.S. PATENT DOCUMENTS

| | | | |
|---|---|---|---|
| 4,996,325 | 2/1991 | Kristinsson | 548/132 |
| 5,179,094 | 1/1993 | Kristiansen et al. | 514/242 |
| 5,354,755 | 10/1994 | Takasugi et al. | 514/259 |

FOREIGN PATENT DOCUMENTS 604365  6/1994  European Pat. Off.

OTHER PUBLICATIONS

M.J. Kornet, *Synthesis of 3-Amino-3,4-dihydro-2(1H)-quinazolinones as Potential Anticonvulsants*, Journal of Heterocyclic Chemistry, vol. 21, No. 6, Nov. 1984, pp. 1709-1711.

*Primary Examiner*—Matthew V. Grumbling
*Attorney, Agent, or Firm*—Cushman Darby & Cushman IP Group of Pillsbury Madison & Sutro LLP

[57] ABSTRACT

There are disclosed a compound represented by the general formula (I):

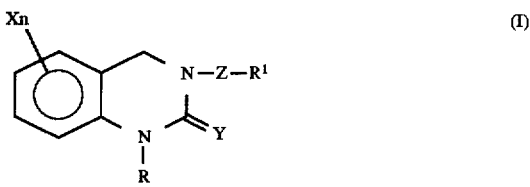

(wherein R, $R^1$, X, Y and n are as defined in the specification), a pest controller containing said compound as an active ingredient, a pest control method using said controller, and an intermediate for producing the compound of the above general formula (I).

6 Claims, No Drawings

SUBSTITUTED AMINOQUINAZOLINONE (THIONE) DERIVATIVES OR SALTS THEREOF, INTERMEDIATES THEREOF, AND PEST CONTROLLERS AND A METHOD FOR USING THE SAME

BACKGROUND OF THE INVENTION

1. Field of the Invention

The present invention relates to substituted aminoquinazolinone (thione) derivatives represented by the general formula (I), or salts thereof:

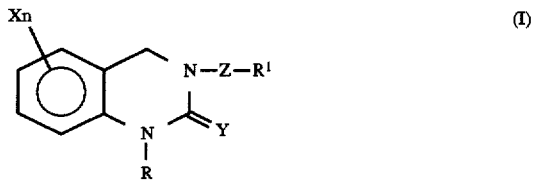

[wherein R is a hydrogen atom; a hydroxyl group; a formyl group; a $(C_{1-12})$alkyl group; a halo$(C_{1-6})$alkyl group; a hydroxy$(C_{1-6})$alkyl group; a $(C_{2-6})$alkenyl group; a $(C_{2-6})$alkynyl group; a $(C_{1-6})$alkoxy group; a halo$(C_{1-6})$alkoxy group; a $(C_{1-6})$alkoxy$(C_{1-3})$alkyl group; a $(C_{1-6})$alkoxy$(C_{1-3})$alkoxy$(C_{1-3})$alkyl group; a $(C_{1-6})$alkylthio group; a halo$(C_{1-6})$alkylthio group; a $(C_{1-6})$alkylsulfinyl group; a $(C_{1-6})$alkylsulfonyl group; a $(C_{1-6})$alkylthio$(C_{1-3})$alkyl group; a di$(C_{1-6})$alkoxy$(C_{1-3})$alkyl group in which the $(C_{1-6})$alkoxy groups may be the same or different; an unsubstituted amino$(C_{1-6})$alkyl group; a substituted amino$(C_{1-6})$alkyl group having one or two substituents which may be the same or different and are selected from the group consisting of $(C_{1-6})$alkyl groups, halo$(C_{1-6})$alkyl groups, $(C_{2-6})$alkenyl groups and $(C_{2-6})$alkynyl groups; a cyano$(C_{1-6})$alkyl group; a $(C_{1-6})$alkylcarbonyl group; a $(C_{1-6})$alkoxycarbonyl group; a hydroxycarbonyl$(C_{1-3})$alkyl group; a $(C_{1-6})$alkoxycarbonyl$(C_{1-3})$alkyl group; an unsubstituted aminocarbonyl group; a substituted aminocarbonyl group having one or two substituents which may be the same or different and are selected from the group consisting of $(C_{1-6})$alkyl groups, $(C_{2-6})$alkenyl groups and $(C_{2-6})$alkynyl groups; a $(C_{3-6})$cycloalkyl$(C_{1-3})$alkyl group; an unsubstituted phenyl$(C_{1-3})$alkyl group; a substituted phenyl$(C_{1-3})$alkyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenylcarbonyl group; a substituted phenylcarbonyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenylthio group; a substituted phenylthio group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenylsulfonyl group; a substituted phenylsulfonyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyl$(C_{1-6})$alkylsulfonyl group; a substituted phenyl$(C_{1-6})$alkylsulfonyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyloxycarbonyl group; a substituted phenyloxycarbonyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$ alkoxy groups, halo$(C_{1-6})$alkoxy groups, $(C_{1-6})$alkylthio groups and halo$(C_{1-6})$alkylthio groups; an unsubstituted phenyloxy $(C_{1-3})$alkyl group; a substituted phenyloxy$(C_{1-3})$alkyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted pheny$(C_{2-6})$alkenyl group; a substituted phenyl$(C_{2-6})$alkenyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$ alkoxy groups, alkylthio groups, halo$(C_{1-6})$alkylthio groups and $(C_{1-2})$alkylenedioxy groups; a phenyl$(C_{2-6})$alkynyl group; a substituted phenyl$(C_{2-4})$alkynyl$(C_{1-3})$alkyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$ alkoxy groups, $(C_{1-6})$alkylthio groups, halo$(C_{1-6})$alkylthio groups and $(C_{1-2})$alkylenedioxy groups; a 1,3-dioxolan-2-yl $(C_{1-3})$alkyl group; or a phthalimido$(C_{1-6})$alkyl group. $R^1$ is a 5- or 6-membered heterocyclic ring having 1 to 3 heteroatoms which may be the same or different and are selected from the group consisting of oxygen atom, sulfur atom and nitrogen atom, said heterocyclic ring being able to have 1 to 5 substituents which may be the same or different and are selected from the group consisting of halogen atoms, cyano group, $(C_{1-6})$alkyl groups, halo$(C_{1-6})$alkyl groups and $(C_{1-6})$alkoxy groups, and the nitrogen atom in the heterocyclic ring being able to form an N-oxide group. Y is an oxygen atom or a sulfur atom. Z is $$-N=C(R^2)-$$

(wherein $R^2$ is a hydrogen atom, a $(C_{1-6})$alkyl group or a halo$(C_{1-6})$alkyl group), $$-N(R^3)-CH(R^2)-$$

(wherein $R^2$ is as defined above, and $R^3$ is a hydrogen atom, a $(C_{1-6})$alkyl group, a formyl group, a $(C_{1-3})$alkylcarbonyl group, a halo$(C_{1-3})$alkylcarbonyl group or a $(C_{1-3})$alkyldithiocarbonyl group), or $$-N(R^3)-CO-$$

(wherein $R^3$ is as defined above), X's, which may be the same or different, are halogen atoms; hydroxyl groups; nitro groups; cyano groups; $(C_{1-6})$alkyl groups; halo$(C_{1-6})$alkyl groups; $(C_{1-6})$alkoxy groups; halo$(C_{1-6})$alkoxy groups; $(C_{1-3})$alkylenedioxy groups; hydroxycarbonyl groups; $(C_{1-6})$alkoxycarbonyl groups; $(C_{2-6})$alkenyloxycarbonyl groups; $(C_{2-6})$alkynyloxycarbonyl groups; unsubstituted aminocarbonyl groups; substituted aminocarbonyl groups having one or two substituents which may be the same or different and are selected from the group consisting of $(C_{1-6})$alkyl groups, alkenyl groups and $(C_{2-6})$alkynyl groups; unsubstituted amino groups; or substituted amino groups having one or two substituents which may be the same or different and are selected from the group consisting of $(C_{1-6})$alkyl groups, $(C_{2-6})$alkenyl groups and $(C_{2-6})$ alkynyl groups, and n is an integer of 0 or 1 to 4], intermediates of said derivatives, i.e., compounds represented by the general formula (II):

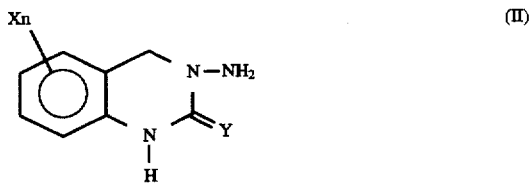

[wherein X's, which may be the same or different, are halogen atoms; hydroxyl groups; nitro groups; cyano groups; $(C_{1-6})$alkyl groups; halo$(C_{1-6})$alkyl groups; $(C_{1-6})$ alkoxy groups; halo$(C_{1-6})$alkoxy groups; $(C_{1-3})$ alkylenedioxy groups; hydroxycarbonyl groups; alkoxycarbonyl groups; $(C_{2-6})$alkenyloxycarbonyl groups; $(C_{2-6})$ alkynyloxycarbonyl groups; unsubstituted aminocarbonyl groups; substituted aminocarbonyl groups having one or two substituents which may be the same or different and are selected from the group consisting of $(C_{1-6})$alkyl groups, $(C_{2-6})$alkenyl groups and alkynyl groups; unsubstituted amino groups; substituted amino groups having one or two substituents which may be the same or different and are selected from the group consisting of $(C_{1-6})$alkyl groups, $(C_{2-6})$alkenyl groups and $(C_{2-6})$alkynyl groups, n is an integer of 0 or 1 to 4, and Y is an oxygen atom or a sulfur atom], pest controllers containing the substituted aminoquinazolinone (thione) derivative as an active ingredient, and a method for using the pest controller.

2. Related Art

Japanese Patent Unexamined Publication Nos. 1-132580, 2-290871 and 6-234748 disclose that triazinone derivatives or imidazole derivatives are useful as pest controllers.

SUMMARY OF THE INVENTION

The present inventors earnestly investigated for developing a novel pest controller and have consequently accomplished the present invention. The present inventive substituted aminoquinazolinone (thione) derivatives of the general formula (I) and compounds of the general formula (II), intermediates for producing the derivatives are novel compounds not known in any literature. Furthermore, the substituted aminoquinazolinone (thione) derivatives of the general formula (I) or salts thereof have an excellent insecticidal effect on various insect pests at low dosage.

DETAILED DESCRIPTION OF THE INVENTION

The present invention relates to substituted aminoquinazolinone (thione) derivatives of the general formula (I), pest controllers containing said derivative as an active ingredient, a method for controlling the pests by the use of said controller, and intermediates for producing the derivatives.

In the definition of the substituents of the substituted aminoquinazolinone (thione) derivative of the general formula (I) of the present invention, the halogen atom includes chlorine atom, bromine atom, iodine atom and fluorine atom. The term "$(C_{1-12})$alkyl group" means a linear or branched alkyl group of 1 to 12 carbon atoms, such as methyl, ethyl, n-propyl, i-propyl, n-butyl, i-butyl, s-butyl, t-butyl, n-pentyl, n-hexyl, n-heptyl, n-octyl, n-nonyl, n-decyl, n-undecyl, n-dodecyl, etc. The term "halo$(C_{1-6})$ alkyl group" means a substituted and linear or branched alkyl group of 1 to 12 carbon atoms having as the substituent (s) one or more halogen atoms which may be the same or different. The term "$(C_{2-6})$alkenyl group" means a linear or branched alkenyl group of 2 to 6 carbon atoms having one or more double bonds. The term "halo$(C_{2-6})$alkenyl group" means a substituted and linear or branched alkenyl group of 2 to 6 carbon atoms having as the substituent(s) one or more halogen atoms which may be the same or different. The term "$(C_{2-6})$alkynyl group" means a linear or branched alkynyl group of 2 to 6 carbon atoms having one or more triple bonds. The term "halo$(C_{2-6})$alkynyl group" means a substituted and linear or branched alkynyl group of 2 to 6 carbon atoms having as the substituent(s) one or more halogen atoms which may be the same or different.

The term "5- or 6-membered heterocyclic ring having 1 to 3 heteroatoms which may be the same or different and are selected from the group consisting of oxygen atom, sulfur atom and nitrogen atom" means any heterocyclic ring derived from furan, thiophene, pyrrole, oxazole, thiazole, isothiazole, pyrazole, imidazole, 1,2,3-thiadiazole, 1,2,4-thiadiazole, 1,2,5-thiadiazole, 1,3,4-thiadiazole, 1,2,4-triazole, pyridine, pyridazine, pyrimidine, pyrazine, pyrrolidine, piperidine, morpholine, thiomorpholine, dithiolane, dithian, piperazine, dioxolan, imidazolizine, tetrahydrofuran and the like.

The substituents of the substituted aminoquinazolinone (thione) derivative of the general formula (I) are preferably as follows: R is a formyl group, a $(C_{1-6})$alkyl group, a $(C_{2-6})$alkenyl group, a $(C_{2-6})$alkynyl group, a $(C_{1-6})$ alkylcarbonyl group, a $(C_{1-6})$alkoxycarbonyl group, a $(C_{1-6})$alkylthio group, a halo$(C_{1-6})$alkylthio group, an unsubstituted phenylcarbonyl group, a substituted phenylcarbonyl group, a substituted phenyl$(C_{1-6})$alkyl group, a substituted phenyl$(C_{1-6})$alkenyl group or a substituted phenyl$(C_{2-6})$alkynyl group; $R^1$ is a pyridyl group, in particular, a 3-pyridyl group; Y is an oxygen atom or a sulfur atom; Z is

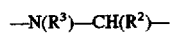

$$-N(R^3)-CH(R^2)-$$

(wherein each of $R^3$ and $R^2$ is a hydrogen atom or a $(C_{1-6})$alkyl group); each of X's is a halogen atom, a $(C_{1-6})$ alkyl group or a methylenedioxy group; and n is 0 to 2.

As the salt of the substituted aminoquinazolinone (thione) derivative of the general formula (I), there can be exemplified salts with mineral acids such as hydrochloric acid, sulfuric acid, nitric acid, etc., and salts with alkali metal atoms such as sodium, potassium, etc.

The compound of the general formula (II), an intermediate used for producing the substituted aminoquinazolinone (thione) derivative of the present invention can be produced by either of the following processes.

Production process 1

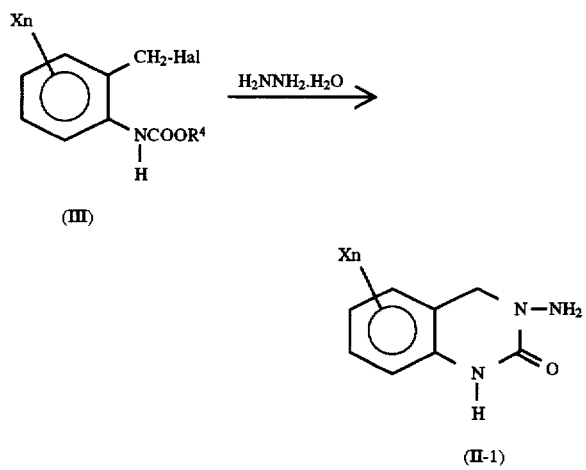

(II-1)

wherein X and n are as defined above, $R^4$ is a $(C_{1-6})$alkyl group, and Hal is a halogen atom.

A compound of the general formula (II-1) can be produced by reacting a compound of the above general formula (III) with hydrazine hydrate in the presence of an inert solvent.

As the inert solvent usable in this reaction, any inert solvent may be used so long as it does not markedly inhibit the progress of the reaction. There can be exemplified alcohols such as methanol, ethanol, propanol, butanol, etc.; halogenated hydrocarbons such as dichloromethane, chloroform, carbon tetrachloride, etc.; aromatic hydrocarbons such as benzene, toluene, xylene, etc.; nitriles such as acetonitrile, benzonitrile, etc.; Cellosolves such as Methyl Cellosolve, etc.; ethers such as diethyl ether, diglyme, dioxane, tetrahydrofuran, etc.; amides such as dimethylformamide, dimethylacetamide, 1,3-dimethyl-2-imidazolidinone, 1-methyl-2-pyrrolidone, etc.; dimethyl sulfoxide; sulfolane; and water. These inert solvents may be used singly or as a mixture thereof.

The reaction temperature may be properly chosen in the range of room temperature to the boiling point of the inert solvent used, and ranges preferably from room temperature to 90° C.

Since the reaction is an equimolar reaction, it is sufficient that the compound of the general formula (III) and hydrazine hydrate are used in equimolar amounts, though either of these reactants may be used in excess. It is preferable to use hydrazine hydrate in excess.

Although the reaction time is varied depending on the scale of reaction, the reaction temperature, etc., it ranges from several minutes to 48 hours.

After completion of the reaction, the desired compound is isolated from the reaction mixture containing the desired compound by a conventional method, and if necessary, purified by recrystallization, dry column chromatography, etc., whereby the desired compound can be produced.

The compound of the above general formula (III) can be produced according to Collect. Czech. Chem. Commn. (Vol. 55), 752 (1990).

Production process 2

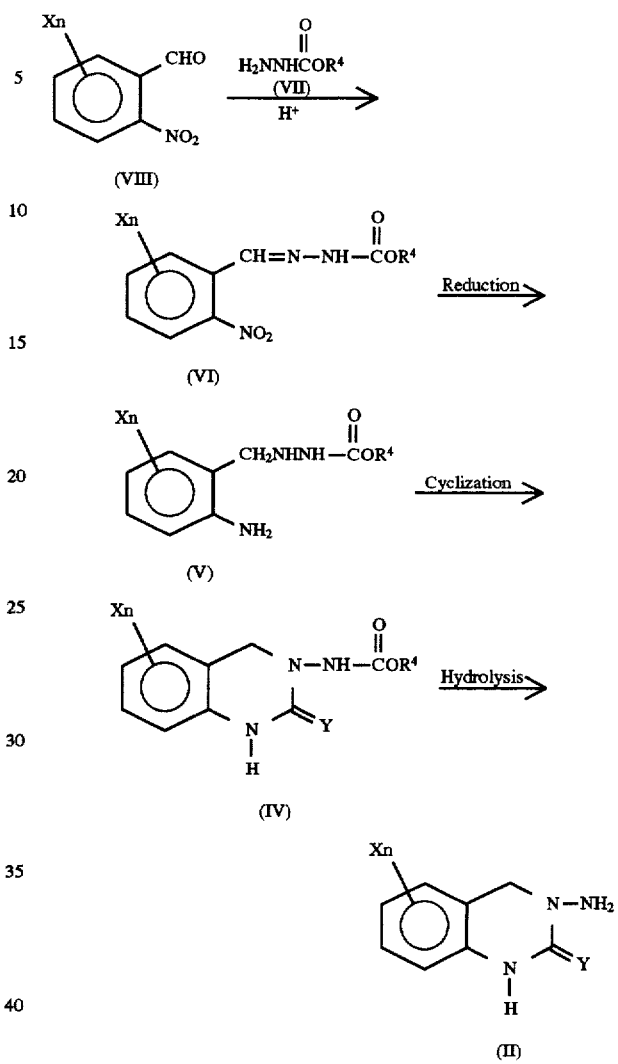

wherein $R^4$, X, Y and n are as defined above. 2-1. General formula (VIII) →general formula (VI)

A compound of the general formula (VI) can be produced by reacting a compound of the general formula (VIII) with a compound of the general formula (VII) in the presence of an inert solvent and a catalyst.

As the inert solvent usable in this reaction, there can be used, for example, the inert solvents exemplified in production process 1. These inert solvents may be used singly or as a mixture thereof.

As the catalyst, there can be used inorganic acids (e.g. hydrochloric acid and sulfuric acid), acetic acid, p-toluenesulfonic acid, etc. The amount of the catalyst used may be such that the catalyst is present in the reaction system in an amount of 0.001 wt % to 10 wt % based on the weight of the compound of the general formula (VIII).

Since the reaction is an equimolar reaction, it is sufficient that the compound of the general formula (VIII) and the compound of the general formula (VII) are used in equimolar amounts, though either of these reactants may be used in excess.

The reaction temperature may be properly chosen in the range of room temperature to the boiling point of the inert solvent used, and ranges preferably from room temperature to 90° C.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

The compound of the general formula (VIII) may be a commercially available one or may be produced by nitrating a substituted benzaldehyde. 2-2. General formula (VI) →general formula (V)

A compound of the general formula (V) can be produced by reducing the compound of the general formula (VI) with a reducing agent or by catalytic reduction in the presence or absence of an inert solvent.

As the reducing agent, there can be used, for example, metal hydrides such as, $NaBH_3CN$, $LiBH_3CN$, etc. and reducing agents such as $BH_3$, etc. The amount of the reducing agent used may be properly chosen in the range of 1 mole to excess moles (in terms of the number of moles of hydride as reducing agent) per mole of the compound of the general formula (VI).

As the inert solvent usable in the reaction, any inert solvent may be used so long as it does not markedly inhibit the progress of the reaction. There can be exemplified alcohols such as methanol, ethanol, propanol, butanol, etc.; Cellosolves such as Methyl Cellosolve, etc.; ethers such as diethyl ether, diglyme, dioxane, tetrahydrofuran, etc.; esters such as ethyl acetate, etc.; amides such as dimethylformamide, dimethylacetamide, 1,3-dimethyl-2-imidazolidinone, 1-methyl-2-pyrrolidone, etc.; dimethyl sulfoxide; sulfolane; and water. These inert solvents may be used singly or as a mixture thereof.

The reaction is carried out under acidic or neutral conditions in the pH range of 1 to 7, preferably 4 to 6. It is sufficient that the pH is adjusted by adding hydrogen chloride, hydrogen bromide or the like to the reaction system.

The reaction temperature is chosen in the range of 0° C. to the boiling point of the solvent, and ranges preferably from room temperature to 70° C.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

When catalytic reduction is carried out as the reduction reaction, it is carried out according to, for example, the method described in Shin Jikken Kagaku Koza, Vol. 15–11, Maruzen Co., Ltd. As the inert solvent usable in this case, there can be exemplified alcohols such as methanol, ethanol, propanol, butanol, etc.; Cellosolves such as Methyl Cellosolve, etc.; ethers such as diethyl ether, diglyme, dioxane, tetrahydrofuran, etc.; hydrocarbons such as hexane, cyclohexane, etc.; fatty acids or esters thereof, such as acetic acid, ethyl acetate, etc.; amides such as dimethylformamide, dimethylacetamide, 1,3-dimethyl-2-imidazolidinone, 1-methyl-2-pyrrolidone, etc.; and ureas such as tetramethylurea, etc. These inert solvents may be used singly or as a mixture thereof.

As the catalyst used in the reduction reaction, there can be exemplified typical catalysts for catalytic reduction, such as palladium-carbon, palladium black, platinum dioxide, Raney nickel, etc. The amount of the catalyst used may be properly chosen in the range of 0.1% molar equivalent to 5% molar equivalent, preferably 0.5% molar equivalent to 1% molar equivalent, relative to the compound of the general formula (VI).

The hydrogen pressure in the reaction ranges from atmospheric pressure to 300 atmospheres, preferably from atmospheric pressure to 50 atmospheres.

The reaction temperature may be properly chosen in the range of room temperature to the boiling point of the inert solvent used, and ranges preferably from room temperature to 70° C.

Although the reaction time is varied depending on the scale of reaction, the reaction temperature, etc., it ranges from several minutes to 48 hours.

After completion of the reaction, the reaction mixture containing the desired compound is treated in the same manner as in the case of using the reducing agent, whereby the desired compound can be produced. 2-3. General formula (V)→general formula (IV)

A compound of the general formula (IV) can be produced by reacting the compound of the general formula (V) with 1,1'-carbonylbis-1H-imidazole (CDI), an alkoxycarbonyl halide, phosgene or thiophosgen in the presence of an inert solvent and in the presence or absence of a base.

As the inert solvent usable in the reaction, there can be exemplified ethers such as diethyl ether, diglyme, dioxane, tetrahydrofuran, etc., and aromatic hydrocarbons such as benzene, toluene, xylene, etc. These inert solvents may be used singly or as a mixture thereof.

As the base, an inorganic base or an organic base may be used, and there can be exemplified inorganic bases such as hydroxides and carbonates of alkali metals and alkaline earth metals [e.g. sodium hydroxide, potassium hydroxide, magnesium hydroxide, sodium carbonate, sodium hydrogencarbonate and potassium carbonate], triethylamine and pyridine. When CDI is used as a reactant, the reaction can be carried out without a base.

The amount of the base used is 2 moles or more per mole of the compound of the general formula (V).

The reaction temperature may be properly chosen in the range of room temperature to the boiling point of the inert solvent used, and ranges preferably from room temperature to 100° C.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced. 2-4. General formula (IV) →general formula (II)

A compound of the general formula (II) can be produced by hydrolyzing the compound of the general formula (IV) by the use of an alkali in the presence of an inert solvent.

As the inert solvent usable in this reaction, there can be exemplified alcohols such as methanol, ethanol, propanol, butanol, etc.; aromatic hydrocarbons such as benzene, toluene, xylene, etc.; ethers such as diethyl ether, diglyme, dioxane, tetrahydrofuran, etc.; and water. These inert solvents may be used singly or as a mixture thereof.

As the base, there can be used hydroxides of alkali metals or alkaline earth metals, such as sodium hydroxide, potassium hydroxide, magnesium hydroxide, etc.

Depending on the alkyl group for $R^4$, the reaction can be carried out also under acidic conditions by using an organic or inorganic acid such as trifluoroacetic acid or hydrochloric acid.

The reaction temperature may be properly chosen in the range of 0° C. to the boiling point of the inert solvent used.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

Typical examples of the compounds of the general formula (II) produced by production processes 1 and 2 are given in Table 1 but they are not intended in any way to limit the scope of the present invention.

General formula (II)

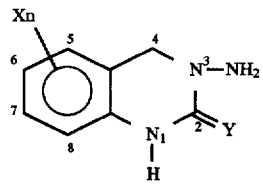

TABLE 1

| No. | Xn | Y | Physical property |
|---|---|---|---|
| II-1 | H | O | m.p. 178.4–183.5° C. |
| II-2 | 5-Cl | O | |
| II-3 | 6-Cl | O | m.p. 210.1° C. |
| II-4 | 7-Cl | O | m.p. 215.1° C. |
| II-5 | 8-Cl | O | |
| II-6 | 5-F | O | m.p. 183° C. |
| II-7 | 6-F | O | m.p. 236.4–238.1° C. |
| II-8 | 7-F | O | |
| II-9 | 8-F | O | |
| II-10 | 5-CH$_3$ | O | |
| II-11 | 6-CH$_3$ | O | m.p. 190.3° C. |
| II-12 | 7-CH$_3$ | O | |
| II-13 | 8-CH$_3$ | O | |
| II-14 | 5-OCH$_3$ | O | |
| II-15 | 6-OCH$_3$ | O | |
| II-16 | 7-OCH$_3$ | O | |
| II-17 | 8-OCH$_3$ | O | m.p. 173.0° C. |
| II-18 | 5-CF$_3$ | O | |
| II-19 | 6-CF$_3$ | O | |
| II-20 | 7-CF$_3$ | O | |
| II-21 | 8-CF$_3$ | O | |
| II-22 | 5-NO$_2$ | O | |
| II-23 | 6-NO$_2$ | O | |
| II-24 | 7-NO$_2$ | O | |
| II-25 | 8-NO$_2$ | O | |
| II-26 | 5-CN | O | |
| II-27 | 6-CN | O | |
| II-28 | 7-CN | O | |
| II-29 | 8-CN | O | |
| II-30 | 5-COOCH$_3$ | O | |
| II-31 | 6-COOCH$_3$ | O | |
| II-32 | 7-COOCH$_3$ | O | |
| II-33 | 8-COOCH$_3$ | O | |
| II-34 | 5-CONHCH$_3$ | O | |
| II-35 | 6-CONHCH$_3$ | O | |
| II-36 | 7-CONHCH$_3$ | O | |
| II-37 | 8-CONHCH$_3$ | O | |
| II-38 | 5-CON(CH$_3$)$_2$ | O | |
| II-39 | 6-CON(CH$_3$)$_2$ | O | |
| II-40 | 7-CON(CH$_3$)$_2$ | O | |
| II-41 | 8-CON(CH$_3$)$_2$ | O | |
| II-42 | 6,7-(OCH$_3$)$_2$ | O | |
| II-43 | 6-OCH$_2$O-7 | O | m.p. 211.0° C. |
| II-44 | 6,7-Cl$_2$ | O | |
| II-45 | 6,7-(CH$_3$)$_2$ | O | |
| II-46 | 6,7-F$_2$ | O | |
| II-47 | H | S | m.p. 174.0° C. |
| II-48 | 5-Cl | S | |
| II-49 | 6-Cl | S | |
| II-50 | 7-Cl | S | |
| II-51 | 8-Cl | S | |

TABLE 1-continued

| No. | Xn | Y | Physical property |
|---|---|---|---|
| II-52 | 5-F | S | |
| II-53 | 6-F | S | |
| II-54 | 7-F | S | |
| II-55 | 8-F | S | |
| II-56 | 5-CH$_3$ | S | |
| II-57 | 6-CH$_3$ | S | |
| II-58 | 7-CH$_3$ | S | |
| II-59 | 8-CH$_3$ | S | |
| II-60 | 5-OCH$_3$ | S | |
| II-61 | 6-OCH$_3$ | S | |
| II-62 | 7-OCH$_3$ | S | |
| II-63 | 8-OCH$_3$ | S | |
| II-64 | 5-CF$_3$ | S | |
| II-65 | 6-CF$_3$ | S | |
| II-66 | 7-CF$_3$ | S | |
| II-67 | 8-CF$_3$ | S | |
| II-68 | 5-NO$_2$ | S | |
| II-69 | 6-NO$_2$ | S | |
| II-70 | 7-NO$_2$ | S | |
| II-71 | 8-NO$_2$ | S | |
| II-72 | 5-CN | S | |
| II-73 | 6-CN | S | |
| II-74 | 7-CN | S | |
| II-75 | 8-CN | S | |
| II-76 | 5-COOCH$_3$ | S | |
| II-77 | 6-COOCH$_3$ | S | |
| II-78 | 7-COOCH$_3$ | S | |
| II-79 | 8-COOCH$_3$ | S | |
| II-80 | 5-CONHCH$_3$ | S | |
| II-81 | 6-CONHCH$_3$ | S | |
| II-82 | 7-CONHCH$_3$ | S | |
| II-83 | 8-CONHCH$_3$ | S | |
| II-84 | 5-CON(CH$_3$)$_2$ | S | |
| II-85 | 6-CON(CH$_3$)$_2$ | S | |
| II-86 | 7-CON(CH$_3$)$_2$ | S | |
| II-87 | 8-CON(CH$_3$)$_2$ | S | |
| II-88 | 6,7-(OCH$_3$)$_2$ | S | |
| II-89 | 6-OCH$_2$O-7 | S | |
| II-90 | 6,7-Cl$_2$ | S | |
| II-91 | 6,7-(CH$_3$)$_2$ | S | |
| II-92 | 6,7-F$_2$ | S | |
| II-93 | 5-OCF$_3$ | O | |
| II-94 | 6-OCF$_3$ | O | |
| II-95 | 7-OCF$_3$ | O | |
| II-96 | 8-OCF$_3$ | O | |
| II-97 | 5-OCF$_3$ | S | |
| II-98 | 6-OCF$_3$ | S | |
| II-99 | 7-OCF$_3$ | S | |
| II-100 | 8-OCF$_3$ | S | |

Typical examples of process for producing the aminoquinazolinone (thione) derivative of the general formula (I) or salt thereof of the present invention are schematically shown below.

Production process 3

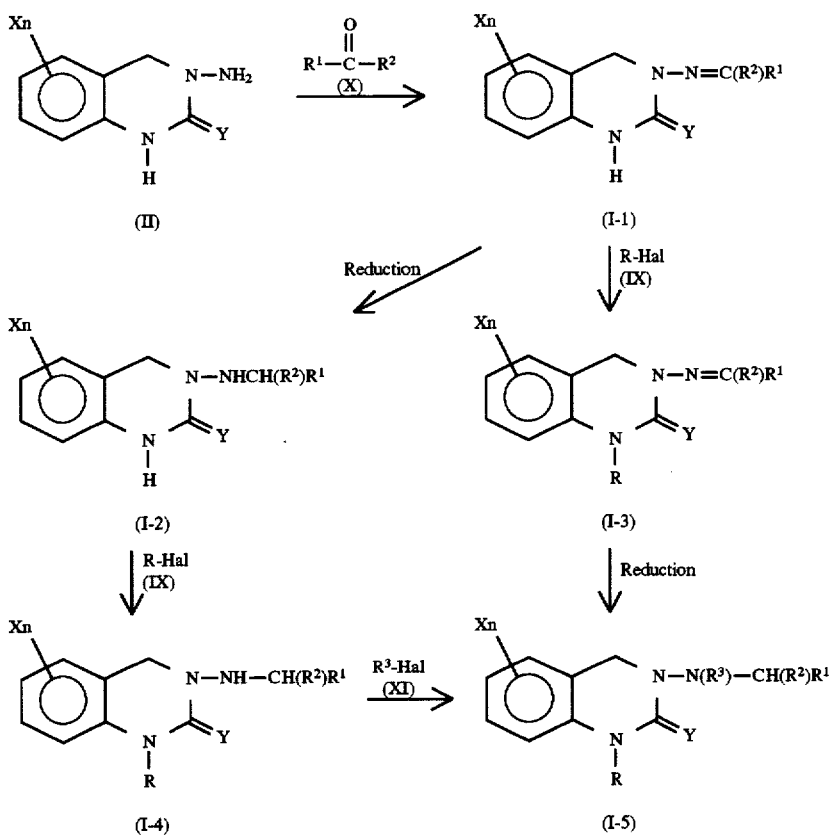

wherein R, $R^1$, $R^2$, $R^3$, X, n and Y are as defined above except that each of R and $R^3$ is not a hydrogen atom, and Hal is halogen atom.

3-1. General formula (II)→general formula (I-1)

An aminoquinazolinone (thione) derivative of the general formula (I-1) can be produced by reacting a compound of the general formula (II) with a compound of the general formula (X) in the presence of an inert solvent and a catalyst.

In the case of this reaction, the desired compound can be produced in a manner similar to that described in production process 2-1.

3-2. General formula (I-1)→general formula (I-3)

An aminoquinazolinone (thione) derivative of the general formula (I-2) can be produced by reacting the aminoquinazolinone (thione) derivative of the general formula (I-1) with a compound of the general formula (IX) in the presence or absence of an inert solvent and a base.

As the inert solvent usable in this reaction, there can be used, for example, the inert solvents exemplified in production process 1.

As the base, an inorganic base or an organic base may be used. In addition to the inorganic or organic bases exemplified in production process 2-3, there can also be used alkoxides such as $CH_3ONa$, $C_2H_5ONa$, $t-C_4H_9ONa$, $C_3OK$, $C_2H_5OK$, $t-C_4H_9OK$, etc., and alkali metal hydrides such as NaH, etc. The amount of the base used may be properly chosen in the range of 1 mole to excess moles per mole of the aminoquinazolinone (thione) derivative of the general formula (I-1).

The reaction temperature may be chosen in the range of 0° C. to the boiling point of the inert solvent used, and ranges preferably from room temperature to 70° C.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

3-3. General formula (I-3)→general formula (I-5)

An aminoquinazolinone (thione) derivative of the general formula (I-4) can be produced by reducing the aminoquinazolinone (thione) derivative of the general formula (I-5) with a reducing agent or by catalytic reduction in the presence or absence of an inert solvent.

In the case of this reaction, the desired compound can be produced in a manner similar to that described in production process 2-2.

3-4. General formula (I-1)→General formula (I-2)

In the case of this reaction, the desired compound can be produced in a manner similar to that described in production process 3-3.

3-5. General formula (I-2)→General formula (I-4)

In the case of this reaction, the desired compound can be produced in a manner similar to that described in production process 3-2.

-6. General formula (I-4)→general formula (I-5)

An aminoquinazolinone (thione) derivative of the general formula (I-5) can be produced by reacting the aminoquinazolinone (thione) derivative of the general formula (I-4) with a compound of the general formula (XI) in the presence or absence of an inert solvent and a base.

Production process 4

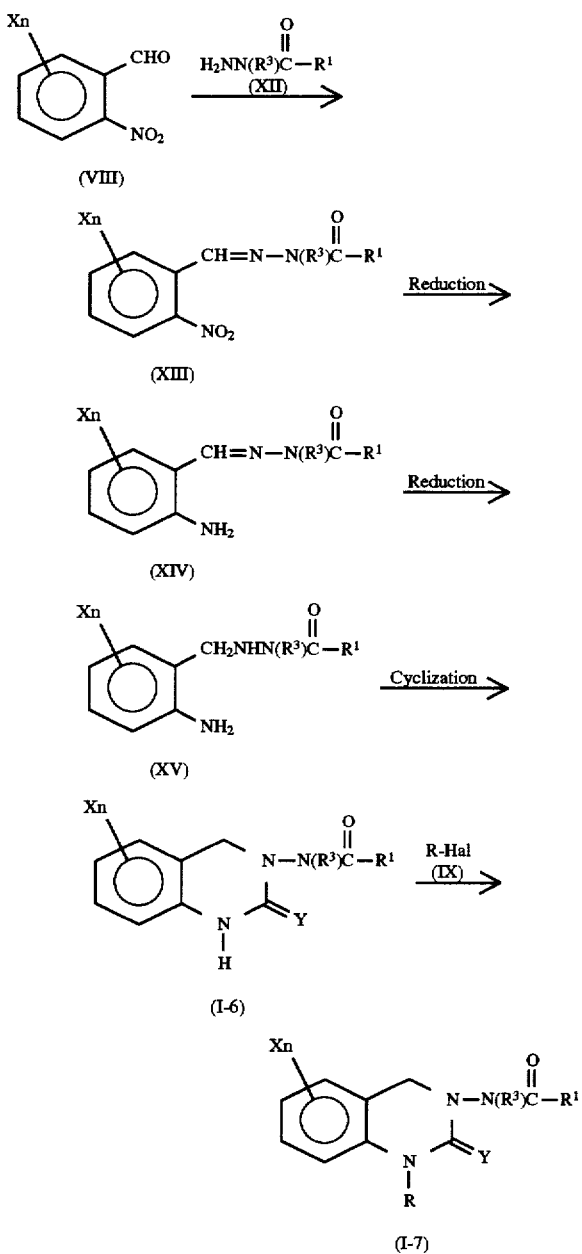

wherein R, R¹, R³, X, Y, Hal and n are as defined above except that R is not a hydrogen atom.

4-1. General formula (VIII)→general formula (XIII)

A compound of the general formula (XIII) can be produced by reacting a compound of the general formula (VIII) with a compound of the general formula (XII) in the presence of an inert solvent and a catalyst.

In the case of this reaction, the desired compound can be produced in a manner similar to that described in production process 2-1.

4-2. General formula (XIII)→general formula (XIV)

A compound of the general formula (XIV) can be produced by reducing the compound of the general formula (XIII) with a reducing agent or by catalytic reduction in the presence or absence of an inert solvent.

In the case of this reaction, the desired compound can be produced in a manner similar to that described in production process 2-2.

4-3. General formula (XIV)→general formula (XV)

A compound of the general formula (XV) can be produced by reducing the compound of the general formula (XIV) with a reducing agent or by catalytic reduction in the presence or absence of an inert solvent.

In the case of this reaction, the desired compound can be produced in a manner similar to that described in production process 2-2.

4-4. General formula (XV)→general formula (I-6)

An aminoquinazolinone (thione) derivative of the general formula (I-6) can be produced by reacting the compound of the general formula (XV) with 1,1'-carbonylbis-1H-imidazole (CDI), an alkoxycarbonyl halide, phosgene or thiophosgene in the presence of an inert solvent and in the presence or absence of a base.

In the case of this reaction, the desired compound can be produced in a manner similar to that described in production process 2-3.

4-5. General formula (I-6)→general formula (I-7)

An aminoquinazolinone (thione) derivative of the general formula (I-7) can be produced by reacting the aminoquinazolinone (thione) derivative of the general formula (I-6) with a compound of the general formula (IX) in the presence or absence of an inert solvent and a base.

In the case of this reaction, the desired compound can be produced in a manner similar to that described in production process 3-2.

Typical examples of the aminoquinazolinone (thione) derivative of the formula (I) or salt thereof of the present invention are given in Table 2 but they are not intended in any way to limit the scope of the present invention.

The abbreviations in Table 2, Table 4 and Table 6 stand for the following substituents:

Ph: phenyl group,
$Q_1$: 2-pyridyl group,
$Q_2$: 3-pyridyl group,
$Q_3$: 4-pyridyl group,
$Q_4$: 2-pyridyl-N-oxide group,
$Q_5$: 3-pyridyl-N-oxide group,
$Q_6$: 4-pyridyl-N-oxide group,
$Q_7$: thiazol-5-yl group,
$Q_8$: furan-2-yl group,
$Q_9$: 1,3-dioxolan-2-yl group,
$Q_{10}$: l phthalimid-1-yl group.

General formula (I')

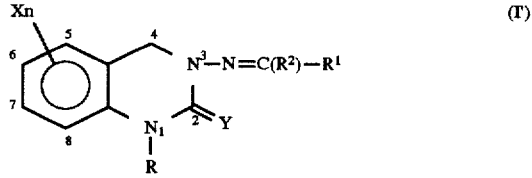

TABLE 2

| No. | R | R¹ | R² | Xn | Y | Physical property |
|---|---|---|---|---|---|---|
| 1 | H | $Q_1$ | H | H | O | m.p. 265.1–266.0° C. |
| 2 | H | $Q_2$ | H | H | O | m.p. 216.6–219.4° C. |
| 3 | H | $Q_2$ | H | H | O | m.p. 220.0° C. (hydrochloride) |
| 4 | H | $Q_3$ | H | H | O | m.p. 214.6–219.5° C. |
| 5 | H | $Q_1$ | $CH_3$ | H | O | m.p. 214.6–219.0° C. |
| 6 | H | $Q_2$ | $CH_3$ | H | O | m.p. 212.4–217.3° C. |
| 7 | H | $Q_3$ | $CH_3$ | H | O | m.p. 241.5–245.1° C. |
| 8 | H | $Q_4$ | H | H | O | |
| 9 | H | $Q_5$ | H | H | O | |
| 10 | H | $Q_6$ | H | H | O | |
| 11 | H | $Q_4$ | $CH_3$ | H | O | |
| 12 | H | $Q_5$ | $CH_3$ | H | O | |
| 13 | H | $Q_6$ | $CH_3$ | H | O | |
| 14 | H | $Q_1$ | H | H | O | |
| 15 | H | 2-Cl-$Q_7$ | H | H | O | |
| 16 | H | 5-$NO_2$-$Q_8$ | H | H | O | m.p. 265.1–266.9° C. |
| 17 | H | 6-Cl-$Q_2$ | H | H | O | m.p. 236.1–240.0° C. |
| 18 | H | $Q_2$ | H | 5-Cl | O | |
| 19 | H | $Q_2$ | H | 6-Cl | O | m.p. 267.9–269.9° C. |
| 20 | H | $Q_2$ | H | 7-Cl | O | m.p. 247.6–250.0° C. |
| 21 | H | $Q_2$ | H | 8-Cl | O | |
| 22 | H | $Q_2$ | $CH_3$ | 5-Cl | O | |
| 23 | H | $Q_2$ | $CH_3$ | 6-Cl | O | |
| 24 | H | $Q_2$ | $CH_3$ | 7-Cl | O | |
| 25 | H | $Q_2$ | $CH_3$ | 8-Cl | O | |
| 26 | H | $Q_2$ | H | 5-F | O | m.p. 251.3–253.1° C. |
| 27 | H | $Q_2$ | H | 6-F | O | m.p. 241.7–243.8° C. |
| 28 | H | $Q_2$ | H | 7-F | O | |
| 29 | H | $Q_2$ | H | 8-F | O | |
| 30 | H | $Q_2$ | $CH_3$ | 5-F | O | |
| 31 | H | $Q_2$ | $CH_3$ | 6-F | O | |
| 32 | H | $Q_2$ | $CH_3$ | 7-F | O | |
| 33 | H | $Q_2$ | $CH_3$ | 8-F | O | |
| 34 | H | $Q_2$ | H | 5-$CH_3$ | O | |
| 35 | H | $Q_2$ | H | 6-$CH_3$ | O | m.p. 237.9–240.2° C. |
| 36 | H | $Q_2$ | H | 7-$CH_3$ | O | |
| 37 | H | $Q_2$ | H | 8-$CH_3$ | O | |
| 38 | H | $Q_2$ | $CH_3$ | 5-$CH_3$ | O | |
| 39 | H | $Q_2$ | $CH_3$ | 6-$CH_3$ | O | |
| 40 | H | $Q_2$ | $CH_3$ | 7-$CH_3$ | O | |
| 41 | H | $Q_2$ | $CH_3$ | 8-$CH_3$ | O | |
| 42 | H | $Q_2$ | H | 5-$OCH_3$ | O | |
| 43 | H | $Q_2$ | H | 6-$OCH_3$ | O | |
| 44 | H | $Q_2$ | H | 7-$OCH_3$ | O | |
| 45 | H | $Q_2$ | H | 8-$OCH_3$ | O | m.p. 198.4–200.1° C. |
| 46 | H | $Q_2$ | $CH_3$ | 5-$OCH_3$ | O | |
| 47 | H | $Q_2$ | $CH_3$ | 6-$OCH_3$ | O | |
| 48 | H | $Q_2$ | $CH_3$ | 7-$OCH_3$ | O | |
| 49 | H | $Q_2$ | $CH_3$ | 8-$OCH_3$ | O | |
| 50 | H | $Q_2$ | H | 5-$CF_3$ | O | |
| 51 | H | $Q_2$ | H | 6-$CF_3$ | O | |
| 52 | H | $Q_2$ | H | 7-$CF_3$ | O | |
| 53 | H | $Q_2$ | H | 8-$CF_3$ | O | |
| 54 | H | $Q_2$ | $CH_3$ | 5-$CF_3$ | O | |
| 55 | H | $Q_2$ | $CH_3$ | 6-$CF_3$ | O | |
| 56 | H | $Q_2$ | $CH_3$ | 7-$CF_3$ | O | |
| 57 | H | $Q_2$ | $CH_3$ | 8-$CF_3$ | O | |
| 58 | H | $Q_2$ | H | 5-$NO_2$ | O | |
| 59 | H | $Q_2$ | H | 6-$NO_2$ | O | |
| 60 | H | $Q_2$ | H | 7-$NO_2$ | O | |
| 61 | H | $Q_2$ | H | 8-$NO_2$ | O | |
| 62 | H | $Q_2$ | $CH_3$ | 5-$NO_2$ | O | |
| 63 | H | $Q_2$ | $CH_3$ | 6-$NO_2$ | O | |
| 64 | H | $Q_2$ | $CH_3$ | 7-$NO_2$ | O | |
| 65 | H | $Q_2$ | $CH_3$ | 8-$NO_2$ | O | |
| 66 | H | $Q_2$ | H | 5-CN | O | |
| 67 | H | $Q_2$ | H | 6-CN | O | |
| 68 | H | $Q_2$ | H | 7-CN | O | |
| 69 | H | $Q_2$ | H | 8-CN | O | |
| 70 | H | $Q_2$ | $CH_3$ | 5-CN | O | |
| 71 | H | $Q_2$ | $CH_3$ | 6-CN | O | |
| 72 | H | $Q_2$ | $CH_3$ | 7-CN | O | |
| 73 | H | $Q_2$ | $CH_3$ | 8-CN | O | |
| 74 | H | $Q_2$ | H | 5-$COOCH_3$ | O | |
| 75 | H | $Q_2$ | H | 6-$COOCH_3$ | O | |
| 76 | H | $Q_2$ | H | 7-$COOCH_3$ | 6 | |

TABLE 2-continued

| No. | R | R$^1$ | R$^2$ | Xn | Y | Physical property |
|---|---|---|---|---|---|---|
| 77 | H | Q$_2$ | H | 8-COOCH$_3$ | O | |
| 78 | H | Q$_2$ | CH$_3$ | 5-COOCH$_3$ | O | |
| 79 | H | Q$_2$ | CH$_3$ | 6-COOCH$_3$ | O | |
| 80 | H | Q$_2$ | CH$_3$ | 7-COOCH$_3$ | O | |
| 81 | H | Q$_2$ | CH$_3$ | 8-COOCH$_3$ | O | |
| 82 | H | Q$_2$ | H | 5-CONHCH$_3$ | O | |
| 83 | H | Q$_2$ | H | 6-CONHCH$_3$ | O | |
| 84 | H | Q$_2$ | H | 7-CONHCH$_3$ | O | |
| 85 | H | Q$_2$ | H | 8-CONHCH$_3$ | O | |
| 86 | H | Q$_2$ | CH$_3$ | 5-CONHCH$_3$ | O | |
| 87 | H | Q$_2$ | CH$_3$ | 6-CONHCH$_3$ | O | |
| 88 | H | Q$_2$ | CH$_3$ | 7-CONHCH$_3$ | O | |
| 89 | H | Q$_2$ | CH$_3$ | 8-CONHCH$_3$ | O | |
| 90 | H | Q$_2$ | H | 5-CON(CH$_3$)$_2$ | O | |
| 91 | H | Q$_2$ | H | 6-CON(CH$_3$)$_2$ | O | |
| 92 | H | Q$_2$ | H | 7-CON(CH$_3$)$_2$ | O | |
| 93 | H | Q$_2$ | H | 8-CON(CH$_3$)$_2$ | O | |
| 94 | H | Q$_2$ | CH$_3$ | 5-CON(CH$_3$)$_2$ | O | |
| 95 | H | Q$_2$ | CH$_3$ | 6-CON(CH$_3$)$_2$ | O | |
| 96 | H | Q$_2$ | CH$_3$ | 7-CON(CH$_3$)$_2$ | O | |
| 97 | H | Q$_2$ | CH$_3$ | 8-CON(CH$_3$)$_2$ | O | |
| 98 | H | Q$_2$ | H | 6-OCH$_2$O-7 | O | m.p. 272.7° C. |
| 99 | H | Q$_2$ | CH$_3$ | 6-OCH$_2$O-7 | O | |
| 100 | H | Q$_2$ | H | 5,6-Cl$_2$ | O | |
| 101 | H | Q$_2$ | H | 6,7-Cl$_2$ | O | |
| 102 | H | Q$_2$ | H | 7,8-Cl$_2$ | O | |
| 103 | H | Q$_2$ | CH$_3$ | 5,6-Cl$_2$ | O | |
| 104 | H | Q$_2$ | CH$_3$ | 6,7-Cl$_2$ | O | |
| 105 | H | Q$_2$ | CH$_3$ | 7,8-Cl$_2$ | O | |
| 106 | H | Q$_2$ | H | 5,6-F$_2$ | O | |
| 107 | H | Q$_2$ | H | 6,7-F$_2$ | O | |
| 108 | H | Q$_2$ | H | 7,8-F$_2$ | O | |
| 109 | H | Q$_2$ | CH$_3$ | 5,6-F$_2$ | O | |
| 110 | H | Q$_2$ | CH$_3$ | 6,7-F$_2$ | O | |
| 111 | H | Q$_2$ | CH$_3$ | 7,8-F$_2$ | O | |
| 112 | H | Q$_2$ | H | 5,6-(CH$_3$)$_2$ | O | |
| 113 | H | Q$_2$ | H | 6,7-(CH$_3$)$_2$ | O | |
| 114 | H | Q$_2$ | H | 7,8-(CH$_3$)$_2$ | O | |
| 115 | H | Q$_2$ | CH$_3$ | 5,6-(CH$_3$)$_2$ | O | |
| 116 | H | Q$_2$ | CH$_3$ | 6,7-(CH$_3$)$_2$ | O | |
| 117 | H | Q$_2$ | CH$_3$ | 7,8-(CH$_3$)$_2$ | O | |
| 118 | H | Q$_1$ | H | H | S | |
| 119 | H | Q$_2$ | H | H | S | |
| 120 | H | Q$_2$ | H | H | S | m.p. 225.1° C. |
| 121 | H | Q$_3$ | H | H | S | |
| 122 | H | Q$_1$ | CH$_3$ | H | S | |
| 123 | H | Q$_2$ | CH$_3$ | H | S | |
| 124 | H | Q$_3$ | CH$_3$ | H | S | |
| 125 | H | Q$_4$ | H | H | S | |
| 126 | H | Q$_5$ | H | H | S | |
| 127 | H | Q$_6$ | H | H | S | |
| 128 | H | Q$_4$ | CH$_3$ | H | S | |
| 129 | H | Q$_5$ | CH$_3$ | H | S | |
| 130 | H | Q$_6$ | CH$_3$ | H | S | |
| 131 | H | Q$_7$ | H | H | S | |
| 132 | H | 2-Cl-Q$_7$ | H | H | S | |
| 133 | H | 5-NO$_2$-Q$_8$ | H | H | S | |
| 134 | H | 6-Cl-Q$_2$ | H | H | S | |
| 135 | H | Q$_2$ | H | 5-Cl | S | |
| 136 | H | Q$_2$ | H | 6-Cl | S | |
| 137 | H | Q$_2$ | H | 7-Cl | S | |
| 138 | H | Q$_2$ | H | 8-Cl | S | |
| 139 | H | Q$_2$ | CH$_3$ | 5-Cl | S | |
| 140 | H | Q$_2$ | CH$_3$ | 6-Cl | S | |
| 141 | H | Q$_2$ | CH$_3$ | 7-Cl | S | |
| 142 | H | Q$_2$ | CH$_3$ | 8-Cl | S | |
| 143 | H | Q$_2$ | H | 5-F | S | |
| 144 | H | Q$_2$ | H | 6-F | S | |
| 145 | H | Q$_2$ | H | 7-F | S | |
| 146 | H | Q$_2$ | H | 8-F | S | |
| 147 | H | Q$_2$ | CH$_3$ | 5-F | S | |
| 148 | H | Q$_2$ | CH$_3$ | 6-F | S | |
| 149 | H | Q$_2$ | CH$_3$ | 7-F | S | |
| 150 | H | Q$_2$ | CH$_3$ | 8-F | S | |
| 151 | H | Q$_2$ | H | 5-CH$_3$ | S | |
| 152 | H | Q$_2$ | H | 6-CH$_3$ | S | |
| 153 | H | Q$_2$ | H | 7-CH$_3$ | | |

TABLE 2-continued

| No. | R | R¹ | R² | Xn | Y | Physical property |
|---|---|---|---|---|---|---|
| 154 | H | $Q_2$ | H | 8-$CH_3$ | S | |
| 155 | H | $Q_2$ | $CH_3$ | 5-$CH_3$ | S | |
| 156 | H | $Q_2$ | $CH_3$ | 6-$CH_3$ | S | |
| 157 | H | $Q_2$ | $CH_3$ | 7-$CH_3$ | S | |
| 158 | H | $Q_2$ | $CH_3$ | 8-$CH_3$ | S | |
| 159 | H | $Q_2$ | H | 5-$OCH_3$ | S | |
| 160 | H | $Q_2$ | H | 6-$OCH_3$ | S | |
| 161 | H | $Q_2$ | H | 7-$OCH_3$ | S | |
| 162 | H | $Q_2$ | H | 8-$OCH_3$ | S | |
| 163 | H | $Q_2$ | $CH_3$ | 5-$OCH_3$ | S | |
| 164 | H | $Q_2$ | $CH_3$ | 6-$OCH_3$ | S | |
| 165 | H | $Q_2$ | $CH_3$ | 7-$OCH_3$ | S | |
| 166 | H | $Q_2$ | $CH_3$ | 8-$OCH_3$ | S | |
| 167 | H | $Q_2$ | H | 5-$CF_3$ | S | |
| 168 | H | $Q_2$ | H | 6-$CF_3$ | S | |
| 169 | H | $Q_2$ | H | 7-$CF_3$ | S | |
| 170 | H | $Q_2$ | H | 8-$CF_3$ | S | |
| 171 | H | $Q_2$ | $CH_3$ | 5-$CF_3$ | S | |
| 172 | H | $Q_2$ | $CH_3$ | 6-$CF_3$ | S | |
| 173 | H | $Q_2$ | $CH_3$ | 7-$CF_3$ | S | |
| 174 | H | $Q_2$ | $CH_3$ | 8-$CF_3$ | S | |
| 175 | H | $Q_2$ | H | 5-$NO_2$ | S | |
| 176 | H | $Q_2$ | H | 6-$NO_2$ | S | |
| 177 | H | $Q_2$ | H | 7-$NO_2$ | S | |
| 178 | H | $Q_2$ | H | 8-$NO_2$ | S | |
| 179 | H | $Q_2$ | $CH_3$ | 5-$NO_2$ | S | |
| 180 | H | $Q_2$ | $CH_3$ | 6-$NO_2$ | S | |
| 181 | H | $Q_2$ | $CH_3$ | 7-$NO_2$ | S | |
| 182 | H | $Q_2$ | $CH_3$ | 8-$NO_2$ | S | |
| 183 | H | $Q_2$ | H | 5-CN | S | |
| 184 | H | $Q_2$ | H | 6-CN | S | |
| 185 | H | $Q_2$ | H | 7-CN | S | |
| 186 | H | $Q_2$ | H | 8-CN | S | |
| 187 | H | $Q_2$ | $CH_3$ | 5-CN | S | |
| 188 | H | $Q_2$ | $CH_3$ | 6-CN | S | |
| 189 | H | $Q_2$ | $CH_3$ | 7-CN | S | |
| 190 | H | $Q_2$ | $CH_3$ | 8-CN | S | |
| 191 | H | $Q_2$ | H | 5-$COOCH_3$ | S | |
| 192 | H | $Q_2$ | H | 6-$COOCH_3$ | | |
| 193 | H | $Q_2$ | H | 7-$COOCH_3$ | S | |
| 194 | H | $Q_2$ | H | 8-$COOCH_3$ | S | |
| 195 | H | $Q_2$ | $CH_3$ | 5-$COOCH_3$ | S | |
| 196 | H | $Q_2$ | $CH_3$ | 6-$COOCH_3$ | S | |
| 197 | H | $Q_2$ | $CH_3$ | 7-$COOCH_3$ | S | |
| 198 | H | $Q_2$ | $CH_3$ | 8-$COOCH_3$ | S | |
| 199 | H | $Q_2$ | H | 5-$CONHCH_3$ | S | |
| 200 | H | $Q_2$ | H | 6-$CONHCH_3$ | S | |
| 201 | H | $Q_2$ | H | 7-$CONHCH_3$ | S | |
| 202 | H | $Q_2$ | H | 8-$CONHCH_3$ | S | |
| 203 | H | $Q_2$ | $CH_3$ | 5-$CONHCH_3$ | S | |
| 204 | H | $Q_2$ | $CH_3$ | 6-$CONHCH_3$ | S | |
| 205 | H | $Q_2$ | $CH_3$ | 7-$CONHCH_3$ | S | |
| 206 | H | $Q_2$ | $CH_3$ | 8-$CONHCH_3$ | S | |
| 207 | H | $Q_2$ | H | 5-$CONHCH_3$ | S | |
| 208 | H | $Q_2$ | H | 6-$CONHCH_3$ | S | |
| 209 | H | $Q_2$ | H | 7-$CON(CH_3)_2$ | S | |
| 210 | H | $Q_2$ | H | 8-$CON(CH_3)_2$ | S | |
| 211 | H | $Q_2$ | $CH_3$ | 5-$CON(CH_3)_2$ | S | |
| 212 | H | $Q_2$ | $CH_3$ | 6-$CON(CH_3)_2$ | S | |
| 213 | H | $Q_2$ | $CH_3$ | 7-$CON(CH_3)_2$ | S | |
| 214 | H | $Q_2$ | $CH_3$ | 8-$CON(CH_3)_2$ | S | |
| 215 | H | $Q_2$ | H | 6-$OCH_2$O-7 | S | |
| 216 | H | $Q_2$ | $CH_3$ | 6-$OCH_2$O-7 | S | |
| 217 | H | $Q_2$ | H | 5,6-$Cl_2$ | S | |
| 218 | H | $Q_2$ | H | 6,7-$Cl_2$ | S | |
| 219 | H | $Q_2$ | H | 7,8-$Cl_2$ | S | |
| 220 | H | $Q_2$ | $CH_3$ | 5,6-$Cl_2$ | S | |
| 221 | H | $Q_2$ | $CH_3$ | 6,7-$Cl_2$ | S | |
| 222 | H | $Q_2$ | $CH_3$ | 7,8-$Cl_2$ | S | |
| 223 | H | $Q_2$ | H | 5,6-$F_2$ | S | |
| 224 | H | $Q_2$ | H | 6,7-$F_2$ | S | |
| 225 | H | $Q_2$ | H | 7,8-$F_2$ | S | |
| 226 | H | $Q_2$ | $CH_3$ | 5,6-$F_2$ | S | |
| 227 | H | $Q_2$ | $CH_3$ | 6,7-$F_2$ | S | |
| 228 | H | $Q_2$ | $CH_3$ | 7,8-$F_2$ | S | |
| 229 | H | $Q_2$ | H | 5,6-$(CH_3)_2$ | S | |
| 230 | H | $Q_2$ | H | 6,7-$(CH_3)_2$ | S | |

TABLE 2-continued

| No. | R | $R^1$ | $R^2$ | Xn | Y | Physical property |
|---|---|---|---|---|---|---|
| 231 | H | $Q_2$ | H | 7,8-$(CH_3)_2$ | S | |
| 232 | H | $Q_2$ | $CH_3$ | 5,6-$(CH_3)_2$ | S | |
| 233 | H | $Q_2$ | $CH_3$ | 6,7-$(CH_3)_2$ | S | |
| 234 | H | $Q_2$ | $CH_3$ | 7,8-$(CH_3)_2$ | S | |
| 235 | CHO | $Q_2$ | H | H | O | m.p. 199° C. |
| 236 | $CH_3$ | $Q_2$ | H | H | O | m.p. 117° C. |
| 237 | $CH_3$ | $Q_2$ | H | 5-Cl | O | |
| 238 | $CH_3$ | $Q_2$ | H | 6-Cl | O | |
| 239 | $CH_3$ | $Q_2$ | H | 7-Cl | O | |
| 240 | $CH_3$ | $Q_2$ | H | 8-Cl | O | |
| 241 | $CH_3$ | $Q_2$ | H | 5-F | O | |
| 242 | $CH_3$ | $Q_2$ | H | 6-F | O | |
| 243 | $CH_3$ | $Q_2$ | H | 7-F | O | |
| 244 | $CH_3$ | $Q_2$ | H | 8-F | O | |
| 245 | $CH_3$ | $Q_2$ | H | 6-$(OCH_2O)$-7 | O | |
| 246 | $CH_3$ | $Q_2$ | $CH_3$ | H | O | |
| 247 | $CH_3$ | $Q_2$ | $CH_3$ | 5-Cl | O | |
| 248 | $CH_3$ | $Q_2$ | $CH_3$ | 6-Cl | O | |
| 249 | $CH_3$ | $Q_2$ | $CH_3$ | 7-Cl | O | |
| 250 | $CH_3$ | $Q_2$ | $CH_3$ | 8-Cl | O | |
| 251 | $CH_3$ | $Q_2$ | $CH_3$ | 5-F | O | |
| 252 | $CH_3$ | $Q_2$ | $CH_3$ | 6-F | O | |
| 253 | $CH_3$ | $Q_2$ | $CH_3$ | 7-F | O | |
| 254 | $CH_3$ | $Q_2$ | $CH_3$ | 8-F | O | |
| 255 | $CH_3$ | $Q_2$ | $CH_3$ | 6-$(OCH_2O)$-7 | O | |
| 256 | $C_2H_5$ | $Q_2$ | H | H | O | m.p. 104° C. |
| 257 | $C_2H_5$ | $Q_2$ | H | 5-Cl | O | |
| 258 | $C_2H_5$ | $Q_2$ | H | 6-Cl | O | |
| 259 | $C_2H_5$ | $Q_2$ | H | 7-Cl | O | |
| 260 | $C_2H_5$ | $Q_2$ | H | 8-Cl | o. | |
| 261 | $C_2H_5$ | $Q_2$ | H | 6-$(OCH_2O)$-7 | O | |
| 262 | $C_2H_5$ | $Q_2$ | $CH_3$ | H | O | |
| 263 | $C_2H_5$ | $Q_2$ | $CH_3$ | 5-Cl | O | |
| 264 | $C_2H_5$ | $Q_2$ | $CH_3$ | 6-Cl | O | |
| 265 | $C_2H_5$ | $Q_2$ | $CH_3$ | 7-Cl | | |
| 266 | $C_2H_5$ | $Q_2$ | $CH_3$ | 8-Cl | O | |
| 267 | $C_2H_5$ | $Q_2$ | $CH_3$ | 6-$(OCH_2O)$-7 | O | |
| 268 | n-$C_4H_9$ | $Q_2$ | H | H | O | m.p. 93° C. |
| 269 | i-$C_4H_9$ | $Q_2$ | H | H | O | m.p. 83° C. |
| 270 | n-$C_8H_{17}$ | $Q_2$ | H | H | O | m.p. 79° C. |
| 271 | n-$CH_{12}H_{25}$ | $Q_2$ | H | H | O | m.p. 70° C. |
| 272 | $ClCH_2(CH_2)_2$ | $Q_2$ | H | H | O | m.p. 78° C. |
| 273 | $CL_3CS$ | $Q_2$ | H | H | O | m.p. 143° C. |
| 274 | $CH_2=CHCH_2$ | $Q_2$ | H | H | O | m.p. 105° C. |
| 275 | $CH\equiv CCH_2$ | $Q_2$ | H | H | O | m.p. 189° C. |
| 276 | $PhCH_2$ | $Q_2$ | H | H | O | m.p. 165° C. |
| 277 | 4-$CH_3O$-$PhCH_2$ | $Q_2$ | H | H | O | m.p. 137° C. |
| 278 | 4-$CF_3$-$PhCH_2$ | $Q_2$ | H | H | O | m.p. 139° C. |
| 279 | 4-Cl-$PhCH_2$ | $Q_2$ | H | H | O | m.p. 87° C. |
| 280 | 3-Cl-$PhCH_2$ | $Q_2$ | H | H | O | m.p. 149° C. |
| 281 | 2-Cl-$PhCH_2$ | $Q_2$ | H | H | O | m.p. 162° C. |
| 282 | $PhCH_2CH_2$ | $Q_2$ | H | H | O | m.p. 145° C. |
| 283 | $CH_3OCH_2$ | $Q_2$ | H | H | O | m.p. 118° C. |
| 284 | $CH_3CH_2OCH_2$ | $Q_2$ | H | H | O | m.p. 129° C. |
| 285 | $CH_3SCH_2$ | $Q_2$ | H | H | O | m.p. 154° C. |
| 286 | $CH_3O$—CO | $Q_2$ | H | H | O | paste |
| 287 | i-$C_4H_9$—O—CO | $Q_2$ | H | H | O | m.p. 98° C. |
| 288 | HO—$COCH_2$ | $Q_2$ | H | H | O | m.p. >300° C. |
| 289 | $CH_3O$—$COCH_2$ | $Q_2$ | H | H | O | m.p. 92° C. |
| 290 | $HOCH_2CH_2$ | $Q_2$ | H | H | O | m.p. 119° C. |
| 291 | $(CH_3O)_2CHCH_2$ | $Q_2$ | H | H | O | m.p. 104° C. |
| 292 | $NCCH_2$ | $Q_2$ | H | H | O | m.p. 222° C. |
| 293 | $CH_3CH_2O$—CO | $Q_2$ | H | H | O | paste |
| 294 | $CH_3OCH_2CH_2OCH_2$ | $Q_2$ | H | H | O | m.p. 75° C. |
| 295 | $CH_3SO_2$ | $Q_2$ | H | H | O | m.p. 149° C. |
| 296 | 4-Cl-$PhSO_2$ | $Q_2$ | H | H | O | m.p. 175° C. |
| 297 | $PhCH=CHCH_2$ | $Q_2$ | H | H | O | m.p. 95° C. |
| 298 | 4-Cl-Ph-$OCH_2$ | $Q_2$ | H | H | O | m.p. 183° C. |
| 299 | $CH_3$ | $Q_2$ | H | H | O | m.p. 215° C. (hydrochloride) |
| 300 | $Q_9$-$CH_2CH_2$ | $Q_2$ | H | H | O | m.p. 121° C. |
| 301 | H | $Q_1$ | H | H | S | |
| 302 | H | $Q_2$ | H | H | S | m.p. 225.1° C. |
| 303 | H | $Q_3$ | H | H | S | |
| 304 | CHO | $Q_2$ | H | H | S | |
| 305 | $CH_3$ | $Q_2$ | H | H | S | |
| 306 | $CH_3$ | $Q_2$ | H | 5-Cl | S | |

TABLE 2-continued

| No. | R | R¹ | R² | Xn | Y | Physical property |
|---|---|---|---|---|---|---|
| 307 | $CH_3$ | $Q_2$ | H | 6-Cl | S | |
| 308 | $CH_3$ | $Q_2$ | H | 7-Cl | S | |
| 309 | $CH_3$ | $Q_2$ | H | 8-Cl | S | |
| 310 | $CH_3$ | $Q_2$ | H | 5-F | S | |
| 311 | $CH_3$ | $Q_2$ | H | 6-F | S | |
| 312 | $CH_3$ | $Q_2$ | H | 7-F | S | |
| 313 | $CH_3$ | $Q_2$ | H | 8-F | S | |
| 314 | $CH_3$ | $Q_2$ | H | 6-($OCH_2O$)-7 | S | |
| 315 | $CH_3$ | $Q_2$ | $CH_3$ | H | S | |
| 316 | $CH_3$ | $Q_2$ | $CH_3$ | 5-Cl | S | |
| 317 | $CH_3$ | $Q_2$ | $CH_3$ | 6-Cl | S | |
| 318 | $CH_3$ | $Q_2$ | $CH_3$ | 7-Cl | S | |
| 319 | $CH_3$ | $Q_2$ | $CH_3$ | 8-Cl | S | |
| 320 | $CH_3$ | $Q_2$ | $CH_3$ | 5-F | S | |
| 321 | $CH_3$ | $Q_2$ | $CH_3$ | 6-F | S | |
| 322 | $CH_3$ | $Q_2$ | $CH_3$ | 7-F | S | |
| 323 | $CH_3$ | $Q_2$ | $CH_3$ | 8-F | S | |
| 324 | $CH_3$ | $Q_2$ | $CH_3$ | 6-($OCH_2O$)-7 | S | |
| 325 | $C_2H_5$ | $Q_2$ | H | H | S | |
| 326 | $C_2H_5$ | $Q_2$ | H | 5-Cl | S | |
| 327 | $C_2H_5$ | $Q_2$ | H | 6-Cl | | |
| 328 | $C_2H_5$ | $Q_2$ | H | 7-Cl | S | |
| 329 | $C_2H_5$ | $Q_2$ | H | 8-Cl | S | |
| 330 | $C_2H_5$ | $Q_2$ | H | 6-($OCH_2O$)-7 | S | |
| 331 | $C_2H_5$ | $Q_2$ | $CH_3$ | H | S | |
| 332 | $C_2H_5$ | $Q_2$ | $CH_3$ | 5-Cl | S | |
| 333 | $C_2H_5$ | $Q_2$ | $CH_3$ | 6-Cl | S | |
| 334 | $C_2H_5$ | $Q_2$ | $CH_3$ | 7-Cl | S | |
| 335 | $C_2H_5$ | $Q_2$ | $CH_3$ | 8-Cl | S | |
| 336 | $C_2H_5$ | $Q_2$ | $CH_3$ | 6-($OCH_2O$)-7 | S | |
| 337 | n-$C_4H_9$ | $Q_2$ | H | H | S | |
| 338 | i-$C_4H_9$ | $Q_2$ | H | H | S | |
| 339 | n-$C_8H_{17}$ | $Q_2$ | H | H | S | |
| 340 | n-$C_{12}H_{25}$ | $Q_2$ | H | H | S | |
| 341 | $ClCH_2(CH_2)_2$ | $Q_2$ | H | H | S | |
| 342 | $Cl_3CS$ | $Q_2$ | H | H | S | |
| 343 | $CH_2=CHCH_2$ | $Q_2$ | H | H | S | |
| 344 | $CH\equiv CCH_2$ | $Q_2$ | H | H | S | |
| 345 | $PhCH_2$ | $Q_2$ | H | H | S | |
| 346 | 4-$CH_3O$-$PhCH_2$ | $Q_2$ | H | H | S | |
| 347 | 4-$CF_3$-$PhCH_2$ | $Q_2$ | H | H | S | |
| 348 | 4-Cl-$PhCH_2$ | $Q_2$ | H | H | S | |
| 349 | 3-Cl-$PhCH_2$ | $Q_2$ | H | H | S | |
| 350 | 2-Cl-$PhCH_2$ | $Q_2$ | H | H | S | |
| 351 | $PhCH_2CH_2$ | $Q_2$ | H | H | S | |
| 352 | $CH_3OCH_2$ | $Q_2$ | H | H | S | |
| 353 | $CH_3CH_2OCH_2$ | $Q_2$ | H | H | S | |
| 353 | $CH_3SCH_2$ | $Q_2$ | H | H | S | |
| 354 | $CH_3O$—CO | $Q_2$ | H | H | S | |
| 355 | i-$C_4H_9O$—CO | $Q_2$ | H | H | S | |
| 356 | HO—$COCH_2$ | $Q_2$ | H | H | S | |
| 357 | $CH_3O$—$COCH_2$ | $Q_2$ | H | H | S | |
| 358 | $HOCH_2CH_2$ | $Q_2$ | H | H | S | |
| 359 | $(CH_3O)_2CHCH_2$ | $Q_2$ | H | H | S | |
| 360 | $NCCH_2$ | $Q_2$ | H | H | S | |
| 361 | $CH_3CH_2O$—CO | $Q_2$ | H | H | S | |
| 362 | $CH_3OCH_2CH_2OCH_2$ | $Q_2$ | H | H | S | |
| 363 | $CH_3SO_2$ | $Q_2$ | H | H | S | |
| 364 | 4-Cl-$PhSO_2$ | $Q_2$ | H | H | S | |
| 365 | $PhCH=CHCH_2$ | $Q_2$ | H | H | S | |
| 366 | 4-Cl-Ph-$OCH_2$ | $Q_2$ | H | H | S | |
| 367 | $Q_9$-$CH_2CH_2$ | $Q_1$ | H | H | S | |
| 368 | $PhCH_2CH_2CH_2$ | $Q_2$ | H | H | O | paste |
| 369 | p-$CH_3$-phCH=$CHCH_2$ | $Q_2$ | H | H | O | paste |
| 370 | p-t-$C_4H_9$-phCH=$CHCH_2$ | $Q_2$ | H | H | O | m.p. 156° C. |
| 371 | 6-$OCH_2O$-7-ph-CH=$CHCH_2$ | $Q_2$ | H | H | O | paste |
| 372 | p-Cl-phCH=$CHCH_2$ | $Q_2$ | H | H | O | m.p. 98° C. |
| 373 | p-Br-phCH=$CHCH_2$ | $Q_2$ | H | H | O | m.p. 138° C. |
| 374 | p-$CF_3O$-phCH=$CHCH_2$ | $Q_2$ | H | H | O | m.p. 83° C. |
| 375 | phC$\equiv CCH_2$ | $Q_2$ | H | H | O | paste |
| 376 | p-$CF_3O$-phC$\equiv CCH_2$ | $Q_2$ | H | H | O | m.p. 215° C. |
| 377 | n-$C_4H_9$—$CO_2$ | $Q_2$ | H | H | O | m.p. 101° C. |
| 378 | i-$C_3H_7O$—CO | $Q_2$ | H | H | S | m.p. 154° C. |
| 379 | K (salt) | $Q_2$ | H | H | S | m.p. 256° C. |
| 380 | $Q_{10}$ | $Q_2$ | H | H | S | m.p. 226° C. |
| 381 | $CH_3CO$ | $Q_2$ | H | H | S | m.p. 153° C. |
| 382 | $C_2H_5CO$ | $Q_2$ | H | H | S | paste |

TABLE 2-continued

| No. | R | $R^1$ | $R^2$ | Xn | Y | Physical property |
|---|---|---|---|---|---|---|
| 383 | $CH_2CH_2CH_3CO$ | $Q_2$ | H | H | S | paste |
| 384 | p-Cl-phCO | $Q_2$ | H | H | S | m.p. 73° C. |
| 385 | $t-C_4H_9-CO$ | $Q_2$ | H | H | S | m.p. 153° C. |
| 386 | $CH_3S$ | $Q_2$ | H | H | S | m.p. 240° C. |
| 387 | ph-S | $Q_2$ | H | H | O | m.p. 182° C. |

Table 3 shows NMR data of the following compounds listed in Table 2: Compound Nos. 293, 286, 368, 369, 371, 375, 382 and 383.

TABLE 3

| No | $^1$H-NMR [$CDCl_3$/TMS, δ value (ppm)] |
|---|---|
| 293 | 1.38 (3H, t), 4.39 (2H, q), 4.87 (2H, s), 7.1–7.43 (4H, m), 7.69 (1H, r.), 8.07–8.14 (1H, m), 8.60 (1H, br.), 8.84 (1H, s), 9.04 (1H, s). |
| 286 | 3.95 (3H, s), 4.88 (2H, s), 7.18–7.42 (1H, m), 7.72 (1H, br. s), 8.10 (1H, m), 8.61 (1H, m), 8.87 (1H, m), 9.15 (s, 1H, s) |
| 368 | 2.18 (2H, m), 2.78 (2H, t), 4.01 (2H, t), 4.86 (2H, s), 6.78 (1H, d), 7.05 (1H, t), 7.17–7.38 (8H, m), 8.08 (1H, s), 8.28 (1H, m), 8.60 (1H, m), 8.60 (1H, m), 8.87 (1H, m) |
| 369 | 2.32 (3H, s), 4.78 (2H, d), 4.95 (2H, s), 6.29 (1H, dt), 6.62 (1H, d), 7.05–7.39 (1H, m), 8.61 (1H, m), 8.88 (1H, m) |
| 371 | 4.72 (2H, d), 4.91 (2H, s), 5.91 (2H, s), 6.15 (1H, dt), 6.55 (1H, ds), 6.20–7.38 (8H, m), 8.12 (1H, s), 8.26 (1H, m), 8.58 (1H, m), 8.87 (1H, m) |
| 375 | 4.90 (2H, s), 5.00 (2H, s), 7.07–7.45 (10H, m), 8.20–8.30 (2H, m), 8.61 (1H, m), 8.85 (1H, m) |
| 382 | 1.23 (3H, t), 2.98 (2H, g), 4.83 (2H, s), 7.22–7.43 (4H, m), 7.80 (1H, m), 8.15 (1H, m), 8.63 (1H, m), 8.83–8.94 (2H, m) |
| 383 | 0.98 (3H, t), 1.68–1.88 (2H, m), 2.95 (2H, t), 4.82 (2H, s), 7.20–7.41 (4H, m), 7.78 (1H, m), 8.13 (1H, m), 8.62 (1H, m), 8.82–8.93 (2H, m) |

General formula (I")

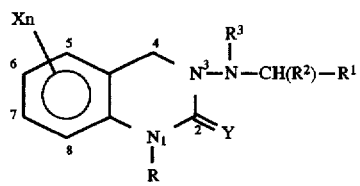

TABLE 4

| No. | R | $R^1$ | $R^2$ | Xn | $R^3$ | Y | Physical property |
|---|---|---|---|---|---|---|---|
| 388 | H | $Q_1$ | H | H | H | O | |
| 389 | H | $Q_2$ | H | H | H | O | m.p. 144.2–150.0° C. |
| 390 | H | $Q_3$ | H | H | H | | |
| 391 | H | $Q_1$ | H | 5-Cl | H | O | |
| 392 | H | $Q_2$ | H | 6-Cl | H | O | |
| 393 | H | $Q_3$ | H | 7-Cl | H | O | |
| 394 | H | $Q_3$ | H | 8-Cl | H | O | |
| 395 | H | $Q_1$ | H | 5-F | H | O | |
| 396 | H | $Q_2$ | H | 6-F | H | O | |
| 397 | H | $Q_3$ | H | 7-F | H | O | |
| 398 | H | $Q_3$ | H | 8-F | H | O | |
| 399 | H | $Q_1$ | $CH_3$ | H | H | O | |
| 400 | H | $Q_2$ | $CH_3$ | H | H | O | |
| 401 | H | $Q_3$ | $CH_3$ | H | H | O | |
| 402 | H | $Q_1$ | $CH_3$ | 5-Cl | H | O | |
| 403 | H | $Q_2$ | $CH_3$ | 6-Cl | H | O | |
| 404 | H | $Q_3$ | $CH_3$ | 7-Cl | H | O | |
| 405 | H | $Q_3$ | $CH_3$ | 8-Cl | H | O | |
| 406 | H | $Q_1$ | $CH_3$ | 5-F | H | O | |
| 407 | H | $Q_2$ | $CH_3$ | 6-F | H | O | |
| 408 | H | $Q_3$ | $CH_3$ | 7-F | H | O | |
| 409 | H | $Q_3$ | $CH_3$ | 8-F | H | O | |
| 410 | $CH_3$ | $Q_1$ | H | H | H | O | |
| 411 | $CH_3$ | $Q_2$ | H | H | H | O | paste |
| 412 | $CH_3$ | $Q_2$ | H | H | H | O | hydrochloride |
| 413 | $CH_3$ | $Q_1$ | H | 5-Cl | H | O | |
| 414 | $CH_3$ | $Q_2$ | H | 6-Cl | H | O | |
| 415 | $CH_3$ | $Q_3$ | H | 7-Cl | H | O | |
| 416 | $CH_3$ | $Q_3$ | H | 8-Cl | H | O | |
| 417 | $CH_3$ | $Q_1$ | H | 5-F | H | O | |
| 418 | $CH_3$ | $Q_2$ | H | 6-F | H | O | |
| 419 | $CH_3$ | $Q_3$ | H | 7-F | H | O | |
| 420 | $CH_3$ | $Q_3$ | H | 8-F | H | O | |
| 421 | $CH_3$ | $Q_3$ | $CH_3$ | H | H | O | |
| 422 | $CH_3$ | $Q_1$ | $CH_3$ | 5-Cl | H | O | |
| 423 | $CH_3$ | $Q_2$ | CH3. | 6-Cl | H | O | |
| 424 | $CH_3$ | $Q_3$ | $CH_3$ | 7-Cl | H | O | |
| 425 | $CH_3$ | $Q_3$ | $CH_3$ | 8-Cl | H | O | |
| 426 | $CH_3$ | $Q_1$ | $CH_3$ | 5-F | H | O | |
| 427 | $CH_3$ | $Q_2$ | $CH_3$ | 6-F | H | O | |
| 428 | $CH_3$ | $Q_3$ | $CH_3$ | 7-F | H | O | |
| 429 | $CH_3$ | $Q_3$ | $CH_3$ | 8-F | H | O | |
| 430 | H | $Q_1$ | H | H | H | S | |
| 431 | H | $Q_2$ | H | H | H | S | |
| 432 | H | $Q_3$ | H | H | H | S | |
| 433 | H | $Q_1$ | H | 5-Cl | H | S | |
| 434 | H | $Q_2$ | H | 6-Cl | H | S | |
| 435 | H | $Q_3$ | H | 7-Cl | H | S | |
| 436 | H | $Q_3$ | H | 8-Cl | H | S | |
| 437 | H | $Q_1$ | H | 5-F | H | S | |
| 438 | H | $Q_2$ | H | 6-F | H | S | |
| 439 | H | $Q_3$ | H | 7-F | H | | |
| 440 | H | $Q_3$ | H | 8-F | H | S | |
| 441 | H | $Q_1$ | $CH_3$ | H | H | S | |
| 442 | H | $Q_2$ | $CH_3$ | H | H | S | |
| 443 | H | $Q_3$ | $CH_3$ | H | H | S | |
| 444 | H | $Q_1$ | $CH_3$ | 5-Cl | H | S | |
| 445 | H | $Q_2$ | $CH_3$ | 6-Cl | H | S | |
| 446 | H | $Q_3$ | $CH_3$ | 7-Cl | H | S | |
| 447 | H | $Q_3$ | $CH_3$ | 8-Cl | H | S | |
| 448 | H | $Q_1$ | $CH_3$ | 5-F | H | S | |
| 449 | H | $Q_2$ | $CH_3$ | 6-F | H | S | |
| 450 | H | $Q_3$ | $CH_3$ | 7-F | H | S | |
| 451 | H | $Q_3$ | $CH_3$ | 8-F | H | S | |
| 452 | $CH_3$ | $Q_1$ | H | H | H | S | |
| 453 | $CH_3$ | $Q_2$ | H | H | H | S | |
| 454 | $CH_3$ | $Q_2$ | H | H | H | S | |
| 455 | $CH_3$ | $Q_1$ | H | 5-Cl | H | S | |
| 456 | $CH_3$ | $Q_2$ | H | 6-Cl | H | S | |
| 457 | $CH_3$ | $Q_3$ | H | 7-Cl | H | S | |
| 458 | $CH_3$ | $Q_3$ | H | 8-Cl | H | S | |
| 459 | $CH_3$ | $Q_1$ | H | 5-F | H | S | |
| 460 | $CH_3$ | $Q_2$ | H | 6-F | H | S | |
| 461 | $CH_3$ | $Q_3$ | H | 7-F | H | S | |

TABLE 4-continued

| No. | R | $R^1$ | $R^2$ | Xn | $R^3$ | Y | Physical property |
|---|---|---|---|---|---|---|---|
| 462 | $CH_3$ | $Q_3$ | H | 8-F | H | S | |
| 463 | $CH_3$ | $Q_3$ | $CH_3$ | H | H | S | |
| 464 | $CH_3$ | $Q_1$ | $CH_3$ | 5-Cl | H | S | |
| 465 | $CH_3$ | $Q_2$ | $CH_3$ | 6-Cl | H | S | |
| 466 | $CH_3$ | $Q_3$ | $CH_3$ | 7-Cl | H | S | |
| 467 | $CH_3$ | $Q_3$ | $CH_3$ | 8-Cl | H | S | |
| 468 | $CH_3$ | $Q_1$ | $CH_3$ | 5-F | H | S | |
| 469 | $CH_3$ | $Q_2$ | $CH_3$ | 6-F | H | S | |
| 470 | $CH_3$ | $Q_3$ | $CH_3$ | 7-F | H | S | |
| 471 | $CH_3$ | $Q_3$ | $CH_3$ | 8-F | H | S | |
| 472 | H | $Q_2$ | H | H | $CH_3CO$ | O | m.p. 72° C. |
| 473 | $CH_3$ | $Q_2$ | H | H | $CH_3CO$ | O | paste |
| 474 | $C_2H_5OCO$ | $Q_2$ | H | H | H | O | m.p. 104° C. |
| 475 | H | $Q_2$ | H | H | HCO | O | paste |
| 476 | i-$C_3H_7OCO$ | $Q_2$ | H | H | H | O | paste |
| 477 | n-$C_4H_9OCO$ | $Q_2$ | H | H | H | O | paste |
| 478 | $CH_3CO$ | $Q_2$ | H | H | H | O | m.p. 59° C. |
| 479 | $C_2H_5CO$ | $Q_2$ | H | H | H | O | m.p. 100° C. |
| 480 | n-$C_3H_7CO$ | $Q_2$ | H | H | H | O | paste |
| 481 | t-$C_4H_9OCO$ | $Q_2$ | H | H | H | O | paste |
| 482 | $CH_3OCO$ | $Q_2$ | H | H | H | O | paste |
| 483 | H | $Q_2$ | H | H | $CF_3CO$ | O | m.p. 186° C. |
| 484 | phCO | $Q_2$ | H | H | H | O | m.p. 133° C. |
| 485 | H | $Q_2$ | H | H | $C_2H_5SCS$ | O | m.p. 181° C. |
| 486 | $CH_3CO$ | $Q_2$ | H | H | $CF_3CO$ | O | past |
| 487 | $C_2H_5OCO$ | $Q_2$ | H | H | $CF_3CO$ | O | paste |
| 488 | p-Cl-phCO | $Q_2$ | H | H | H | O | paste |
| 489 | m-Cl-phCO | $Q_2$ | H | H | H | O | m.p. 181° C. |
| 490 | n-$C_3H_7OCO$ | $Q_2$ | H | H | H | O | paste |
| 491 | $CH_3CO$ | $Q_2$ | H | H | H | O | paste |
| 491.1 | 3-$CH_3O$-ph-CO | $Q_2$ | H | H | H | O | paste |
| 491.2 | 4-$CH_3O$-ph-CO | $Q_2$ | H | H | H | O | paste |
| 491.3 | 2,6-$F_2$-ph-CO | $Q_2$ | H | H | H | O | paste |
| 491.4 | 4-$CF_3$-ph-CO | $Q_2$ | H | H | H | O | m.p. 127° C. |
| 491.5 | 3-$CH_3$-ph-CO | $Q_2$ | H | H | H | O | m.p. 140° C. |
| 491.6 | 3-F-ph-CO | $Q_2$ | H | H | H | O | m.p. 153° C. |

Table 5 shows NMR data of the following compounds listed in Table 4: compound Nos. 411, 473, 475, 476, 477, 480, 481, 482, 486, 487, 488, 490, 491, and 491.1 to 491.3.

TABLE 5

| No | $^1$H-NMR [$CDCl_3$/TMS, δ value (ppm)] |
|---|---|
| 411 | 3.33 (3H, s), 4.01 (2H, br.), 4.36 (2H, s), 5.21 (1H, br. t), 6.84 (1H, br.), 6.92–7.03 (2H, m), 7.19–7.32 (2H, m), 7.68–7.76 (1H, m), 8.51 (1H, br.), 8.62 (1H, s). |
| 473 | 2.06 (3H, s), 3.32 (3H, s), 4.22–5.40 (4H, m), 6.85–7.73 (6H, m), 8.45–8.56 (2H, m) |
| 475 | 4.32–5.24 (4H, m), 6.72–7.31 (6H, m), 8.33 (1H, s), 8.47 (1H, bs) 8.56–8.65 (2H, m) |
| 476 | 1.38 (6H, d), 4.02 (2H, d), 4.25 (2H, s), 5.15 (1H, m), 5.33 (1H, t), 6.81–7.28 (5H, m), 7.53 (1H, m), 8.48–8.50 (2H, m) |
| 477 | 0.95 (3H, t), 1.42 (2H, m), 1.71 (2H, m), 4.01 (2H, d), 4.22 (2H, s), 4.28 (2H, t), 5.31 (1H, t), 6.85–7.58 (6H, m), 8.43–8.50 (2H, m) |
| 480 | 0.99 (3H, t), 1.69–1.78 (2H, m), 2.88 (2H, t), 4.03 (2H, d), 4.25 (2H, d), 5.30 (2H, t), 6.90–7.72 (6H, m), 8.50–8.52 (2H, m) |
| 481 | 1.58 (9H, s), 4.04 (2H, d), 4.26 (2H, s), 5.28 (1H, t), 6.89–7.62 (6H, m), 8.50–8.55 (2H, m) |
| 482 | 3.92 (3H, s), 4.05 (2H, d), 4.26 (2H, s), 5.29 (1H, t), 6.90–7.76 (6H, m), 8.49–8.56 (2H, m) |
| 486 | 2.50 (3H, s), 4.20–5.18 (4H, m), 6.88–7.98 (6H, m), 8.50–8.65 (2H, m) |
| 487 | 1.41 (3H, t), 3.91–5.35 (6H, m), 6.80 (1H, d), 7.12–7.68 (5H, m), 8.47–8.58 (2H, m) |
| 488 | 4.01 (2H, d), 4.52 (2H, s), 5.22 (1H, t), 7.03–7.85 (10H, m), 8.53–8.60 (2H, m) |

TABLE 5-continued

| No | $^1$H-NMR [$CDCl_3$/TMS, δ value (ppm)] |
|---|---|
| 490 | 1.01 (3H, t), 1.75 (2H, m), 4.03 (2H, d), 4.20–4.35 (4H, m), 5.30 (1H, t), 6.85–7.32 (4H, m), 7.55–7.68 (2H, m), 8.45–8.53 (2H, m) |
| 491 | 2.35 (5H, s), 4.21 (2H, s), 4.48 (2H, s), 7.15–7.35 (3H, m), 7.56 (1H, d), 8.01 (1H, m), 8.55 (1H, m), 8.82–8.92 (2H, m) |
| 491.1 | 3.86 (s, 3H), 4.01 (d, 2H), 4.50 (s, 2H), 5.23 (t, 1H), 6.95–7.35 (m, 8H), 7.61–7.73 (m, 2H), 8.45–8.59 (m, 2H) |
| 491.2 | 3.87 (s, 3H), 4.04 (d, 2H), 4.53 (s, 2H), 5.22 (t, 1H), 6.93–7.30 (m, 7H), 7.65–7.85 (m, 3H), 8.50–8.60 (m, 2H) |
| 491.3 | 3.93 (d, 2H), 4.32 (s, 2H), 5.10 (t, 1H), 6.92–7.55 (m, 8H), 8.03 (d, 1H), 8.42–8.55 (m, 2H). |

General formula (I''')

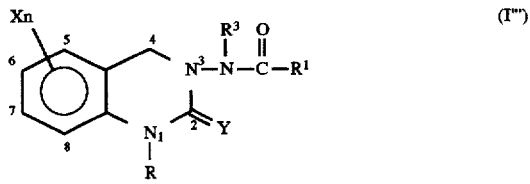

TABLE 6

| No. | R | $R^1$ | Xn | $R^3$ | Y | Physical property |
|---|---|---|---|---|---|---|
| 492 | H | $Q_1$ | H | H | O | |
| 493 | H | $Q_2$ | H | H | O | m.p. 221–224.0° C. |
| 494 | H | $Q_3$ | H | H | O | |
| 495 | H | $Q_1$ | 5-Cl | H | O | |
| 496 | H | $Q_2$ | 6-Cl | H | O | |
| 497 | H | $Q_3$ | 7-Cl | H | O | |
| 498 | H | $Q_3$ | 8-Cl | H | O | |
| 499 | H | $Q_1$ | 5-F | H | O | |
| 500 | H | $Q_2$ | 6-F | H | O | |
| 501 | H | $Q_3$ | 7-F | H | O | |
| 502 | H | $Q_3$ | 8-F | H | O | |
| 503 | H | $Q_1$ | H | H | O | |
| 504 | H | $Q_2$ | H | H | O | |
| 505 | H | $Q_3$ | H | H | O | |
| 506 | H | $Q_1$ | 5-Cl | H | O | |
| 507 | H | $Q_2$ | 6-Cl | H | O | |
| 508 | H | $Q_3$ | 7-Cl | H | O | |
| 509 | H | $Q_3$ | 8-Cl | H | O | |
| 510 | H | $Q_1$ | 5-F | H | O | |
| 511 | H | $Q_2$ | 6-F | H | O | |
| 512 | H | $Q_3$ | 7-F | H | O | |
| 513 | H | $Q_3$ | 8-F | H | O | |
| 514 | $CH_3$ | $Q_1$ | H | H | O | |
| 515 | $CH_3$ | $Q_2$ | H | H | O | |
| 516 | $CH_3$ | $Q_3$ | H | H | O | |
| 517 | $CH_3$ | $Q_1$ | 5-Cl | H | O | |
| 518 | $CH_3$ | $Q_2$ | 6-Cl | H | O | |
| 519 | $CH_3$ | $Q_3$ | 7-Cl | H | O | |
| 520 | $CH_3$ | $Q_3$ | 8-Cl | H | O | |
| 521 | $CH_3$ | $Q_1$ | 5-F | H | O | |
| 522 | $CH_3$ | $Q_2$ | 6-F | H | O | |
| 523 | $CH_3$ | $Q_3$ | 7-F | H | O | |
| 524 | $CH_3$ | $Q_3$ | 8-F | H | O | |
| 525 | $CH_3$ | $Q_3$ | H | H | O | |
| 526 | $CH_3$ | $Q_1$ | 5-Cl | H | O | |
| 527 | $CH_3$ | $Q_2$ | 6-Cl | H | O | |
| 528 | $CH_3$ | $Q_3$ | 7-Cl | H | O | |
| 529 | $CH_3$ | $Q_3$ | 8-Cl | H | O | |
| 530 | $CH_3$ | $Q_1$ | 5-F | H | O | |
| 531 | $CH_3$ | $Q_2$ | 6-F | H | O | |
| 532 | $CH_3$ | $Q_3$ | 7-F | H | O | |
| 533 | $CH_3$ | $Q_3$ | 8-F | H | O | |
| 534 | H | $Q_1$ | H | H | S | |

TABLE 6-continued

| No. | R | R¹ | Xn | R³ | Y | Physical property |
|---|---|---|---|---|---|---|
| 535 | H | Q₂ | H | H | S | |
| 536 | H | Q₃ | H | H | S | |
| 537 | H | Q₁ | 5-Cl | H | S | |
| 538 | H | Q₂ | 6-Cl | H | S | |
| 539 | H | Q₃ | 7-Cl | H | S | |
| 540 | H | Q₃ | 8-Cl | H | S | |
| 541 | H | Q₁ | 5-F | H | S | |
| 542 | H | Q₂ | 6-F | H | S | |
| 543 | H | Q₃ | 7-F | H | S | |
| 544 | H | Q₃ | 8-F | H | S | |
| 545 | H | Q₁ | H | H | S | |
| 546 | H | Q₂ | H | H | S | |
| 547 | H | Q₃ | H | H | S | |
| 548 | H | Q₁ | 5-Cl | H | S | |
| 549 | H | Q₂ | 6-Cl | H | S | |
| 550 | H | Q₃ | 7-Cl | H. | S | |
| 551 | H | Q₃ | 8-Cl | H | S | |
| 552 | H | Q₁ | 5-F | H | S | |
| 553 | H | Q₂ | 6-F | H | S | |
| 554 | R | Q₃ | 7-F | H | S | |
| 555 | H | Q₃ | 8-F | H | S | |
| 556 | CH₃ | Q₁ | H | H | S | |
| 557 | CH₃ | Q₂ | H | H | S | |
| 558 | CH₃ | Q₂ | H | H | S | |
| 559 | CH₃ | Q₁ | 5-Cl | H | S | |
| 560 | CH₃ | Q₂ | 6-Cl | H | S | |
| 561 | CH₃ | Q₃ | 7-Cl | H | S | |
| 562 | CH₃ | Q₃ | 8-Cl | H | S | |
| 563 | CH₃ | Q₁ | 5-F | H | S | |
| 564 | CH₃ | Q₂ | 6-F | H | S | |
| 565 | CH₃ | Q₃ | 7-F | H | S | |
| 566 | CH₃ | Q₃ | 8-F | H | S | |
| 567 | CH₃ | Q₃ | H | H | S | |
| 568 | CH₃ | Q₁ | 5-Cl | H | S | |
| 569 | CH₃ | Q₂ | 6-Cl | H | S | |
| 570 | CH₃ | Q₃ | 7-Cl | H | S | |
| 571 | CH₃ | Q₃ | 8-Cl | H | S | |
| 572 | CH₃ | Q₁ | 5-F | H | S | |
| 573 | CH₃ | Q₂ | 6-F | H | S | |
| 574 | CH₃ | Q₃ | 7-F | H | S | |
| 575 | CH₃ | Q₃ | 8-F | H | S | |

Typical examples of the present invention are described below, but they should not be construed as limiting the scope of the invention.

EXAMPLE 1

Production of 3-amino-3,4-dihydro-2(1H)-quinazolinone (compound No. II-1)

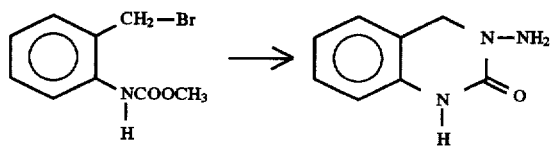

In 20 ml of methanol was dissolved 2.44 g (0.01 mole) of methyl 2-bromomethylphenylcarbamate, after which 5 g (0.1 mole) of hydrazine hydrate was added to the solution and the reaction was carried out with heating under reflux for 3 hours.

After completion of the reaction, the excess hydrazine hydrate and the solvent were removed from the reaction solution containing the desired compound by filtration under reduced pressure to obtain a crude product. The crude product obtained was recrystallized from 95% methanol to obtain 1.55 g of the desired compound.

Physical property: m.p. 178.4–183.5° C.
Yield: 95%.

EXAMPLE 2

Production of methyl 2-(4,5-methylenedioxy-2-nitrophenylmethylidene)carbazate

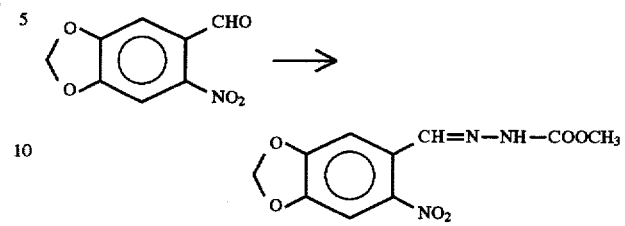

To 20 ml of methanol were added 3.9 g (0.02 mole) of 6-nitropiperonal, methylcarbamic acid and a drop of sulfuric acid, and the reaction was carried out with heating under reflux for 3 hours.

After completion of the reaction, the reaction solution was allowed to cool to room temperature and the crystals precipitated were collected by filtration to obtain 5.1 g of the desired compound.

¹H-NMR [CDCl₃/TMS, δ values (ppm)] 3.80 (3H, s.), 5.8 (2H, s.), 6.3 (1H, s.), 6.5 (1H, s.), 7.7 (1H, br. s.), 7.8 (1H, hr. s.).

Yield: 95%.

2-2. Production of methyl 2-(2-amino-4,5-methylenedioxyphenylmethyl)carbazate

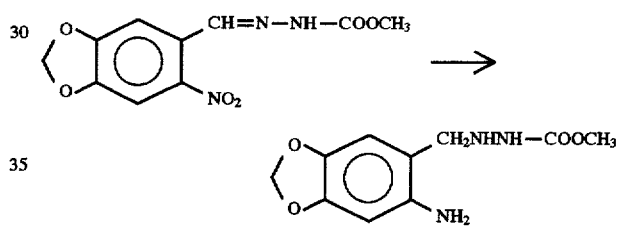

To 100 ml of methanol were added 4.0 g (0.015 mole) of the methyl 2-(4,5-methylenedioxy-2-nitrophenylmethylidene)carbazate obtained in 2-1 and 0.4 g of 5% palladium-carbon, and hydrogenation was carried out at 3 to 4 kg/m².

After the absorption of a theoretical amount of hydrogen, the catalyst was removed from the reaction mixture by filtration and the solvent was distilled off under reduced pressure to obtain 3.6 g of the desired compound.

¹H-NMR [CDCl₃/TMS, δ values (ppm)] 3.73 (3H, s.), 3.90 (2H, s.), 3.6–4.2 (3H, br.), 5.84 (2H, s.), 6.27 (1H, s.), 6.57 (1H, s. ), 6.3 (1H, br.).

Yield: quantitative.

2-3. Production of 3-methoxycarbonylamino-6,7-methylenedioxy-3,4-dihydro-2(1H)-quinazoline

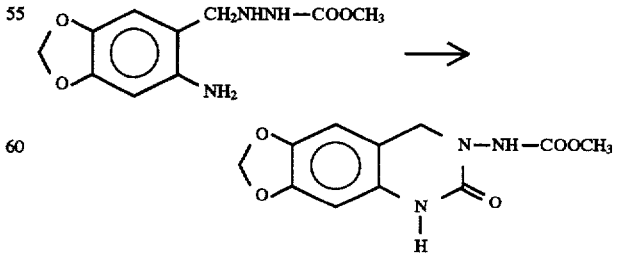

In 20 ml of tetrahydrofuran were dissolved 3.6 g (0.015 mole) of the methyl 2-(2-amino-4,5- methylenedioxyphenylmethyl)carbazate obtained in 2-2 and 2.6 g (0.0165 mole) of 1,1'-carbonylbis-1H-imidazole, and the reaction was carried out at room temperature for 3 hours.

After completion of the reaction, the reaction solution was poured into 20 ml of water and the desired compound was extracted with ethyl acetate. The extracted solution was washed with water and a saturated aqueous sodium chloride solution, dried over anhydrous magnesium sulfate, and then distilled under reduced pressure to remove the solvent, whereby 3.6 g of the desired compound was obtained.

1H-NMR [CDCl$_3$/TMS, δ values (ppm)] 3.7 (3H, s.), 4.37 (2H, s.), 5.93 (2H, s.), 6.0 (1H, s.), 6.6 (1H, s.), 7.4 (1H, s.), 7.7 (1H, s.).

Yield: 90%.

2-4. Production of 3-amino-6,7-methylenedioxy-3,4-dihydro-2(1H)-quinazolinone (compound No. II-43)

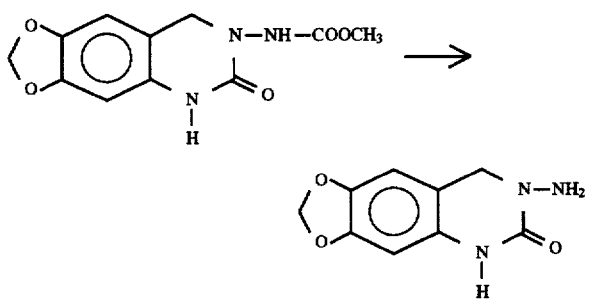

In 20 ml of methanol was dissolved 2.65 g (0.01 mole) of the 3-methoxycarbonylamino-6,7-methylenedioxy- 3,4-dihydro-2(1H)-quinazoline obtained in 2-3, followed by adding thereto 4 ml of a 20% aqueous sodium hydroxide solution, and the reaction was carried out with heating under reflux for 3 hours.

After completion of the reaction, the solvent was distilled off under reduced pressure and water was added to the residue to precipitate crystals. The crystals were collected by filtration and the crude product thus obtained was recrystallized from 95% methanol to obtain 1.3 g of the desired compound. Physical property: m.p. 211.0° C. Yield: 62%.

EXAMPLE 3

3-1. Production of 3-t-butoxycarbonylamino-3,4-dihydro-2 (1H)-quinazolithione

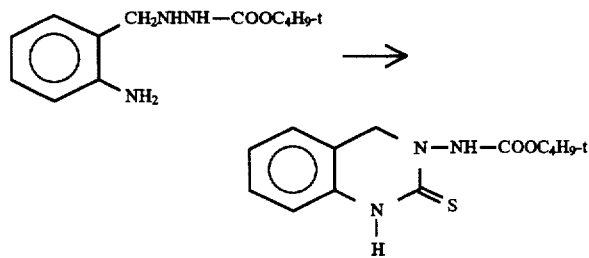

In 20 ml of ether were dissolved 1.38 g (5 mmoles) of t-butyl 2-(2-aminophenylmethyl)carbazate produced in a manner similar to that described in example 2, 2-1 and 2-2 and 1.11 g (11.0 mmoles) of triethylamine, and the solution was cooled to -20° C., after which 1.54 9 (5.25 moles) of thiophosgene was added dropwise to the solution over a period of 30 minutes. After completion of the dropwise addition, the reaction solution was brought to room temperature and the salt precipitated was filtered off. The filtrate was washed with water and a saturated aqueous sodium chloride solution, dried over anhydrous magnesium sulfate, and then distilled under reduced pressure to remove the solvent. The resulting residue was recrystallized from ethyl acetate-ether to obtain 0.5 g of the desired compound.

$^1$H-NMR [CDCl$_3$/TMS, δ values (ppm)] 1.52 (9H, s.), 4.87 (2H, s.), 6.7 (1H, d.), 7.02–7.24 (4H, m.), 8.15 (1H, br. s.).

Yield: 35.8%.

3-2. Production of 3-amino-3,4-dihydro-2(1H)-quinazolithione (compound No. II-47)

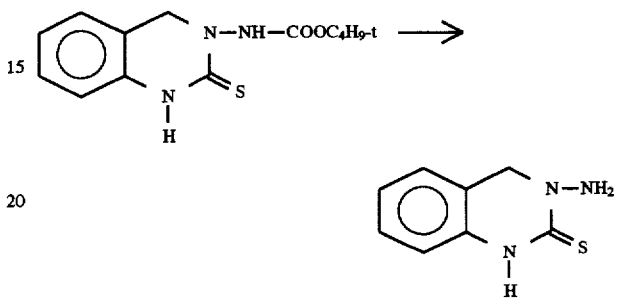

To 2 ml of trifluoroacetic acid was added 0.5 g (1.8 moles) of the 3-t-butoxycarbonylamino-3,4-dihydro-2(1H)-quinazolithione obtained in 3-1, and the reaction was carried out at room temperature for 3 hours.

After completion of the reaction, 10 ml of ethanol was added to the reaction solution and the solvent was distilled off under reduced pressure. The resulting residue was recrystallized from methanol to obtain 0.35 g of the desired compound.

Physical property: m.p. 174.0° C. Yield: 93.1%.

EXAMPLE 4

3-(3-Pyridylmethylideneamino)-3,4-dihydro-2(1H)-quinazolinone (compound No. 2)

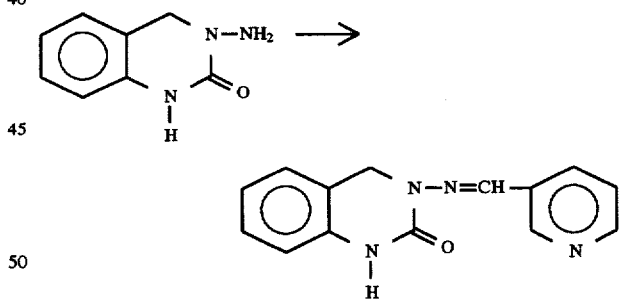

To 10 ml of methanol were added 0.4 g (2.5 mmoles) of 3-amino-3,4-dihydro-2(1H)-quinazoline, 0.27 g (2.5 mmoles) of nicotinic aldehyde and a drop of sulfuric acid, and the reaction was carried out with heating under reflux for 3 hours.

After completion of the reaction, the crystals precipitated in the reaction solution were collected by filtration and dried to obtain 0.58 g of the desired compound.

Physical property: m.p. 216.6–219.4° C.

Yield: 92%.

EXAMPLE 5

3-[1-(3-Pyridylethylideneamino)-3,4-dihydro-2(1H)-quinazolinone (compound No. 6)

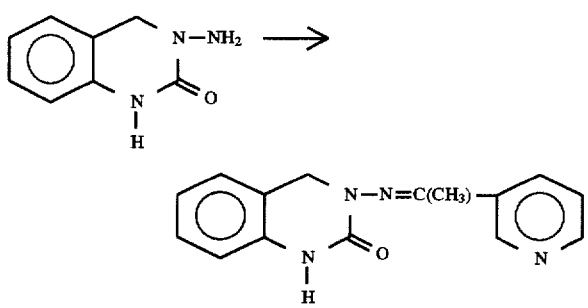

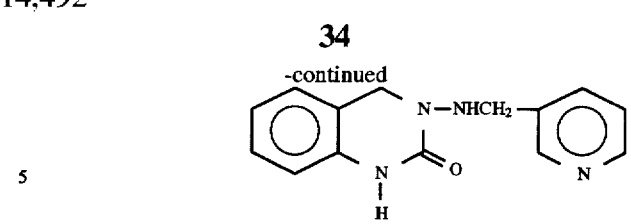

To 10 ml of methanol were added 0.4 g (2.5 mmoles) of 3-amino-3,4-dihydro-2(1H)-quinazolinone, 0.31 g (2.5 mmoles) of 3-acetylpyridine and a drop of sulfuric acid, and the reaction was carried out with heating under reflux for 3 hours.

After completion of the reaction, the crystals precipitated in the reaction solution were collected by filtration and dried to obtain 0.6 g of the desired compound.

Physical property: m.p. 212.4°–217.3° C.

Yield: 90%.

EXAMPLE 6

3-(3-Pyridylmethylideneamino)-3,4-dihydro-2(1H)-quinazolithione (compound No. 120)

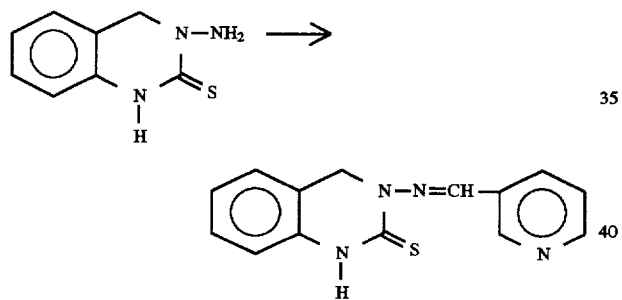

To 10 ml of methanol were added 0.15 g (1.4 mmoles) of 3-amino-3,4-dihydro-2(1H)-quinazolithione, 0.15 g (1.4 mmoles) of nicotinic aldehyde and a drop of sulfuric acid, and the reaction was carried out with heating under reflux for 3 hours.

After completion of the reaction, the crystals precipitated in the reaction solution were collected by filtration and dried to obtain 0.35 g of the desired compound.

Physical property: m.p. 225.1° C. Yield: 94.5%.

EXAMPLE 7

3-(3-Pyridylmethylamino)-3,4-dihydro-2(1H)-quinazolinone (compound No. 409)

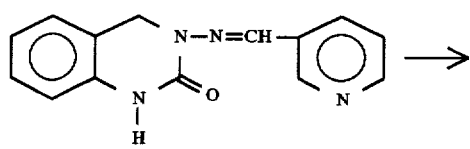

To 50 ml of acetic acid were added 1.26 g (5 mmoles) of 3-(3-pyridylmethylideneamino)-3,4-dihydro-2(1H)-quinazolinone and 0.2 g of 5% palladium-carbon, and hydrogenation was carried out at 3 to 4 kg/m2.

After the absorption of a theoretical amount of hydrogen, the catalyst was removed from the reaction mixture by filtration and the solvent was distilled off under reduced pressure. A 20% aqueous sodium hydroxide solution was added to the residue and the desired compound was extracted with ethyl acetate (20 ml×3). The extracted solution was washed with water and a saturated aqueous sodium chloride solution, dried over anhydrous magnesium sulfate, and then distilled under reduced pressure to remove the solvent. The crude product thus obtained was recrystallized from ethyl acetate-methanol to obtain 1.14 g of the desired compound.

Physical property: m.p. 144.2–150.0° C.

Yield: 90%.

EXAMPLE 8

1-Methyl-3-(3-pyridylmethylideneamino)-3,4-dihydro-2(1H)-quinazolinone (compound No. 236)

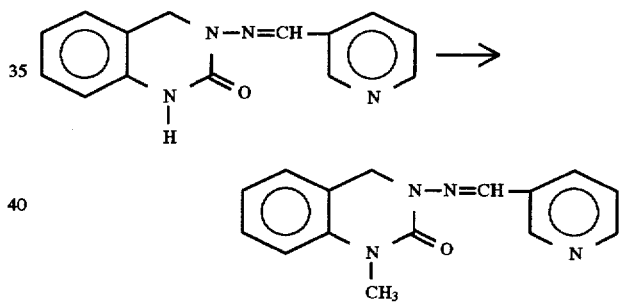

In 20 ml of dimethylformamide was dissolved 1.26 g (5 mmoles) of 3-(3-pyridylmethylideneamino)-3,4-dihydro-2(1H)-quinazolinone, after which 0.21 g of sodium hydride (62.4%) was added to the solution, and the reaction was carried out at room temperature for 30 minutes. Then, 0.85 g (6 mmoles) of methyl iodide was added and the resulting mixture was subjected to reaction for 3 hours.

After completion of the reaction, the reaction mixture was poured into ice water and the desired compound was extracted with ethyl acetate (20 ml×3). The extracted solution was washed with water and a saturated aqueous sodium chloride solution, dried over anhydrous magnesium sulfate, and then distilled under reduced pressure to remove the solvent. The crude product thus obtained was purified by a silica gel column chromatography to obtain 0.67 g of the desired compound.

Physical property: m.p. 117° C. Yield: 50%.

EXAMPLE 9

1-Methyl-3-(3-pyridylmethylamino)-3,4-dihydro-2(1H)-quinazolinone (compound No. 411)

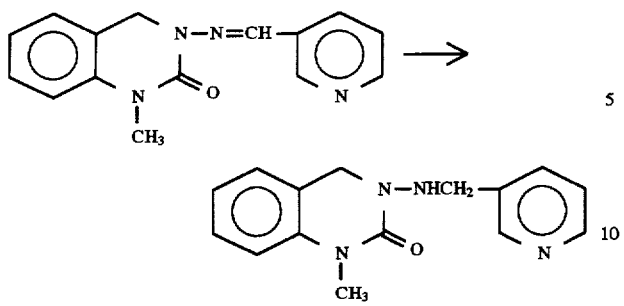

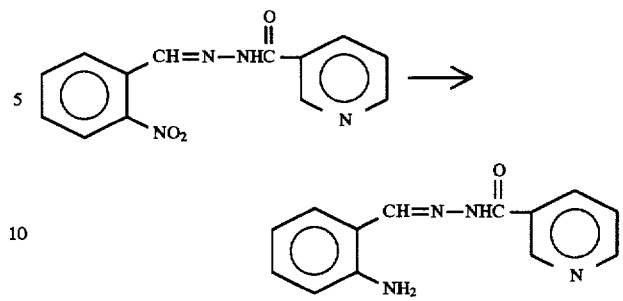

In 10 ml of a 5% methanolic solution of hydrogen chloride was dissolved 0.5 g (1.8 mmoles) of 1-methyl-3-(3-pyridylmethylideneamino)-3,4-dihydro-2(1H) quinazolinone, followed by adding thereto 0.11 g of NaBH₃CN, and the reaction was carried out at room temperature for 3 hours.

After completion of the reaction, the reaction mixture was poured into water and the resulting mixture was adjusted to pH 9 with a 10% aqueous sodium hydroxide solution. The desired compound was extracted with ethyl acetate (20 ml×3), and the extracted solution was washed with water and a saturated aqueous sodium chloride solution, dried over anhydrous magnesium sulfate, and then distilled under reduced pressure to remove the solvent. The crude product thus obtained was recrystallized from ethyl acetate-methanol to obtain 0.15 g of the desired compound.

Physical property: paste. Yield: 30%. ¹H-NMR [CDCl₃/TMS, 6 values (ppm)] 3.33 (3H, s.), 4.01 (3H, br.), 4.36 (2H, s.), 5.21 (1H, br. t.), 6.84 (1H, br.), 6.92–7.03 (2H, m.), 7.19–7.32 (2H, m.), 7.68–7.76 (1H, m.), 8.15 (1H, br.), 8.62 (1H, s.).

EXAMPLE 10

10-1. Production of 2-(2-nitrophenylmethylidene)-nicotinic acid hydrazide

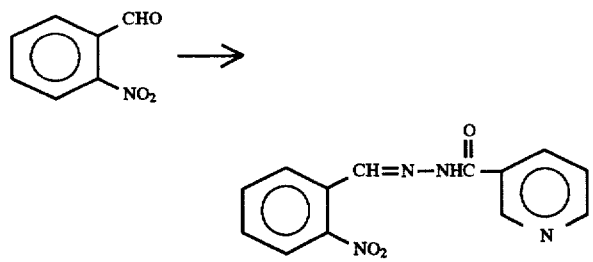

To 20 ml of methanol were added 3.33 g (22 mmoles) of 2-nitrobenzaldehyde, 3.0 g (22 mmoles) of nicotinic acid hydrazide and a drop of a sulfuric acid, and the reaction was carried out with heating under reflux for 3 hours.

After completion of the reaction, the reaction solution was cooled to room temperature and the crystals precipitated were collected by filtration to obtain 5.34 g of the desired compound.

Physical property: m.p. 251° C. Yield: 90%.

10-2. Production of 2-(2-aminophenylmethylidene)nicotinic acid hydrazide

To 20 ml of acetic acid were added 2.7 g (10 mmoles) of the 2-(2-nitrophenylmethylidene)nicotinic acid hydrazide obtained in 10-1 and 0.27 g of 5% palladium-carbon, and hydrogenation was carried out at 3 to 4 kg/m².

After the absorption of a theoretical amount of hydrogen, the catalyst was removed from the reaction mixture by filtration and the solvent was distilled off under reduced pressure to obtain 2.35 g of the desired compound. ¹H-NMR [CDCl₃/TMS, 6 values (ppm)] 6.58 (1H, t.), 6.75 (1H, d.), 7.07 (2H, s.), 7.12 (1H, t.), 7.19 (1H, d.), 7.58 (1H, m.), 8.26 (1H, m.), 8.42 (1H, s.), 8.70 (1H, m.), 9.04 (1H, d.), 11.9 (1H, hr.).

Yield: quantitative.

10-3. Production of 2-(2-aminophenylmethyl)nicotinic acid hydrazide

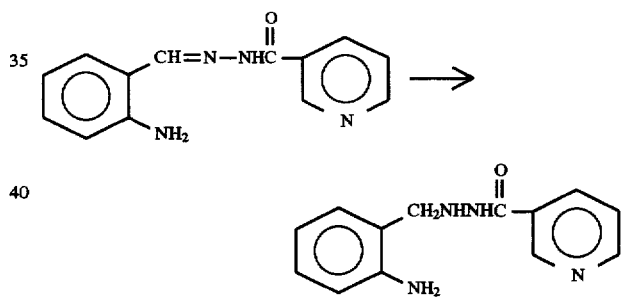

To 10 ml of water were added 1.2 g (5 mmoles) of the 2-(2-aminophenylmethylidene)nicotinic acid hydrazide obtained in 10-2 and 0.38 g (10 mmoles) of NaBH₄, and the reaction was carried out at 60° C for 5 hours.

After completion of the reaction, 10 ml of a 10% aqueous sodium hydroxide solution was added to the reaction mixture, and the desired compound was extracted with ethyl acetate. The extracted solution was washed with water and a saturated aqueous sodium chloride solution, dried over anhydrous magnesium sulfate, and then distilled under reduced pressure to remove the solvent, whereby 0.65 g of the desired compound was obtained.

¹H-NMR [CDCl₃/TMS, δ values (ppm)] 4.1 (2H, s.), 4.5 (2H, br. s.), 5.0 (1H, br. s.), 6.7 (2H, m.), 7.0–7.2 (2H, m.), 7.35–7.4 (1H, m.), 7.97 (1H, s.), 8.03–8.07 (1H, m.), 8.76 (1H, m.), 8.78 (1H, m.).

Yield: 54.1%. 10-4. Production of 3-(3-pyridylcarbonylamino)-3,4-dihydro-2(1H)-quinazoline (compound No. 493)

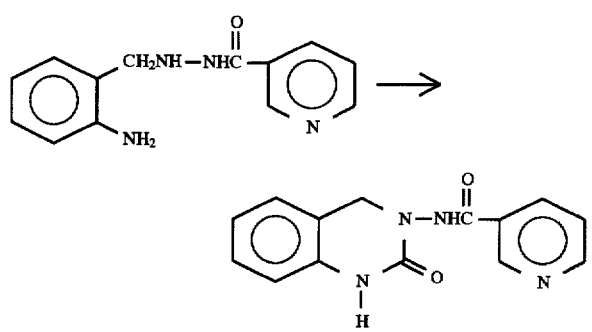

In 10 ml of tetrohydrofuran were dissolved 0.6 g (2.4 mmoles) of the 2-(2-aminophenylmethyl)nicotinic acid hydrazide obtained in 10-3 and 0.38 g (2.4 moles) of 1,1'-carbonylbis-1H-imidazole, and the reaction was carried out at room temperature for 3 hours.

After completion of the reaction, the reaction solution was poured into 20 ml of water and the desired compound was extracted with ethyl acetate. The extracted solution was washed with water and a saturated aqueous sodium chloride solution, dried over anhydrous magnesium sulfate, and then distilled under reduced pressure to remove the solvent. The resulting residue was recrystallized from methanol to obtain 0.5 g of the desired compound.

Physical property: m.p. 221.1°–224.0° C.
Yield: 78.1%.

Pest controllers containing as an active ingredient the substituted aminoquinazolinone (thione) derivative of the general formula (I) or salt thereof of the present invention are suitable for controlling various insect pests such as agricultural insect pests, forest insect pests, horticultural insect pests, stored grain insect pests, sanitary insect pests, nematodes, etc. They have an insecticidal effect also, for example, on HEMIPTERA including tea green leafhopper (*Empoasca onukii*), green rice leafhopper (*Nephotettix cincticeps*), brown rice planthopper (*Nilaparvata lugens*), whitebacked rice planthopper (*Sogatella furcifera*), citrus psylla (*Diaphorina citri*), citrus whitefly (*Dialeurodes citri*), sweetpotato whitefly (*Bemisia tabaci*), greenhouse whitefly (*Trialeurodes vaporariorum*), Cabbage aphid (*Brevicoryne brassicae*), Cotton aphid (*Aphis gossypii*), Wheat aphid (*Rhopalosiphum padi*), green peach aphid (*Myzus persicae*), Indian wax scale (*Ceroplastes ceriferus*), cottony citrus scale (*Pulvinaria aurantii*), camphor scale (*Pseudaonidia duplex*), San Jose scale (*Comstockaspis perniciosa*), arrowhead scale (*Unaspis yanonensis*), etc., and TYLENCHIDA including coffee root-lesion nematode (*Pratylenchus coffeae*), potato cyst nematode (*Globodera rostochiensis*), root-knot nematode (*Meloidogyne sp.*), citrus nematode (*Tylenchulus semipenetrans*), *Aphelenchus sp.* (*Aphelenchus arenas*), chrysanthemum foliar nematode (*Aphelenchoides ritzemabosi*), etc.

The zoological names and the like are in accordance with Applied Zoology and Entomology Society of Japan, "List of Agricultural and Forest Injurious Animals and Insects", published in 1987.

The pest controller containing as an active ingredient the substituted aminoquinazolinone (thione) derivative of the general formula (I) or salt thereof of the present invention has a marked control effect on the above-exemplified insect pests, sanitary pests, and/or nematodes, which are injurious to paddy fields, fruit trees, vegetables and other crops, and flowers and ornamental plants. Therefore, the desired effect of the insecticide of the present invention can be obtained by applying the insecticide to the paddy field water, stalks and leaves of fruit trees, vegetables, other crops, flowers and ornamental plants, soil, etc., or to the inside of a house or ditches around a house, in which the above-exemplified sanitary insect pests injurious to men and beasts appear or are expected to appear. The application is carried out at a season at which the insect pests, sanitary pests or nematodes are expected to appear, before their appearance or at the time when their appearance is confirmed. The present invention however should not be limited to these embodiment.

When the substituted aminoquinazolinone (thione) derivative of the general formula (I) or salt thereof of the present invention is used as a pest controller, the derivative or salt is generally prepared into conveniently usable forms according to an ordinary manner for preparation of agrochemicals.

That is, the substituted aminoquinazolinone (thione) derivative of the general formula (I) or salt thereof of the present invention and, optionally, an adjuvant are blended with a suitable inert carrier in a proper proportion and prepared into a suitable preparation form such as a suspension, emulsifiable concentrate, soluble concentrate, wettable powder, granules, dust or tablets through dissolution, dispersion, suspension, mixing, impregnation, adsorption or sticking.

The inert carrier used in the present invention may be either solid or liquid. As the solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon, i.e. synthetic, high-dispersion silicic acid, also called finely divided hydrated silica or hydrated silicic acid, some of commercially available products contain calcium silicate as the major component), activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalenes; halogenated hydrocarbons such as dichloroethane, chloroform and carbon tetrachloride; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicon oils may also be used as a defoaming agent.

The content of the active ingredient may be varied as required. In dusts or granules, the suitable content thereof is from 0.01 to 50% by weight. In emulsifiable concentrates or flowable wettable powders, it is also from 0.01 to 50% by weight.

The pest controller containing as an active ingredient the substituted aminoquinazolinone (thione) derivative of the general formula (I) or salt thereof of the present invention is used to control a variety of insect pests in the following manner. That is, it is applied to the insect pests or a site where appearance or growth of the insect pests is undesirable, as it is or after being properly diluted with or suspended in water or the like, in an amount effective for control of the insect pests.

The applying dosage of the pest controller containing as an active ingredient the substituted aminoquinazolinone (thione) derivative of the general formula (I) or salt thereof of the present invention is varied depending upon various factors such as a purpose, insect pests to be controlled, a growth state of a plant, tendency of insect pests appearance, weather, environmental conditions, a preparation form, an application method, an application site and application time. It may be properly chosen in the range of 0.1 g to 5 kg (in terms of the active ingredient) per 10 ares depending upon purposes.

The pest controller containing as an active ingredient the substituted aminoquinazolinone (thione) derivative of the general formula (I) or salt thereof of the present invention may be used in admixture with other insecticides or fungicides in order to expand both spectrum of controllable insect pest species and the period of time when effective applications are possible or to reduce the dosage.

Typical formulation examples and test examples of the present invention are described below but they should not be construed as limiting the scope of the invention.

In the formulation examples, parts are all by weight.

Formulation Example 1

| | |
|---|---|
| Each compound listed in Tables 2, 4 and 6 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Tables 2, 4 and 6 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Tables 2, 4 and 6 | 5 parts |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Tables 2, 4 and 6 | 20 parts |
| Mixture of kaolin and synthetic, high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Control efficacy against green peach aphid (Myzus persicae)

A Chinese cabbage plant was planted in each of plastic pots with a diameter of 8 cm and a height of 8 cm and green peach aphids were propagated on the plant, after which the parasites in each pot were counted.

Each substituted aminoquinazolinone (thione) derivative of the general formula (I) or salt thereof of the present invention was dispersed in and diluted with water to obtain a 500 ppm liquid chemical. The stalks and leaves of the potted Chinese cabbage plants were sprayed with the liquid chemical and air-dried, and then the pots were stored in a greenhouse. Six days after the spraying, green peach aphids parasitic on each Chinese cabbage plant were counted and the control efficacy degree was calculated by the following equation, whereby the insecticidal effect was judged according to the criterion shown below.

Control efficacy=100 −{($T \times Ca$)/($Ta \times C$)}×100

Ta: number of parasites before spraying in treated group,

T: number of parasites after spraying in treated group,

Ca: number of parasites before spraying in untreated group,

C: number of parasites after spraying in untreated group.

Criterion

| Efficacy | Percent Control (%) |
|---|---|
| A | 100 |
| B | 99–90 |
| C | 89–80 |
| D | 79–50 |

Test Example 2

Insecticidal effect on brown rice planthopper (*Nilaparvata lugens*)

Each substituted aminoquinazolinone (thione) derivative of the general formula (I) or salt thereof of the present invention was dispersed in and diluted with water to obtain a 500 ppm liquid chemical. Rice seedlings (cultivar: Nihonbare) were immersed in the liquid chemical for 30 seconds and air-dried, after which each seedling was placed in a glass test tube and inoculated with 10 third-instar nymphs of brown rice planthopper, and the test tube was pluged with a cotton plug. Eight days after the inoculation, the dead and alive were counted. The mortality was calculated by the following equation and the control effect was judged according to the criterion described below.

Corrected larval mortality (%)={(Ca/c−Ta/T)/Ca/c}×100

Ta: number of alive nymphs in treated groups

T: number of inoculated nymphs in treated groups

Ca: number of alive numphs in untreated groups c: number of inoculated nymphs in untreated groups Criterion: the same as in Test Example 1

As a result, it was found that when used in a pest controller containing as an active ingredient the substituted aminoquinazolinone (thione) derivative of the general formula (I) or salt thereof of the present invention, the following compounds had an insecticidal effect rated D or higher on green peach aphid: compound Nos. 2, 3, 4, 6, 16, 19, 20, 35, 45, 98, 120, 235, 236, 256, 268, 269, 271, 272, 273, 274, 275, 276, 283, 284, 285, 288, 289, 295, 297, 298, 300, 368, 369, 370, 371, 372, 373, 374, 375, 376, 377, 378, 379, 380, 381, 382, 383, 384, 385, 386, 387, 472, 473, 474, 475, 476, 477, 478, 479, 481, 482, 483, 484, 485, 486, 487, 488, 489, 490, 491 and 491.1 to 491.6. In particular, the following compounds had an excellent insecticidal effect rated A: compound Nos. 2, 3, 4, 6, 16, 19, 20, 35, 98, 120, 235, 236, 256, 268, 269, 271, 272, 273, 274, 275, 276, 283, 284, 285, 288, 289, 295, 297, 298, 300, 368, 369, 370, 371, 372, 373, 374, 375, 376, 377, 378, 379, 380, 381, 382, 383, 384, 385, 386, 387, 473, 474, 475, 476, 477, 478, 479, 481, 482, 483, 484, 485, 486, 487, 488, 489, 490 and 491.

The following compounds had an insecticidal effect rated D or higher on brown rice planthopper: compound Nos. 2, 3, 4, 7, 19, 20, 35, 45, 98, 120, 236, 268, 269, 272, 273, 288, 298, 300, 389, 370, 371, 372, 374, 375, 376, 380, 381, 382, 383, 384, 387, 472, 474, 477, 479, 481, 482, 484, 386, 473, 475, 483, 486, 487, 488, 489, 490 and 491. In particular, the following compounds had an excellent insecticidal effect rated A: compound Nos. 3, 19, 35, 236, 269, 273, 381, 382, 386, 473, 475, 480, 483, 486, 489 and 491.1 to 491.6.

What is claimed is:

1. A substituted aminoquinazolinone (thione) derivative represented by the general formula (I), or a salt thereof:

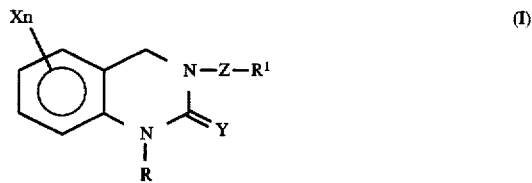

wherein

R is a hydrogen atom; a hydroxyl group; a formyl group; a $(C_{1-12})$alkyl group; a halo$(C_{1-6})$alkyl group; a hydroxy$(C_{1-6})$alkyl group; a $(C_{2-6})$alkenyl group; a $(C_{2-6})$alkynyl group; a $(C_{1-6})$alkoxy group; a halo $(C_{1-6})$alkoxy group; a $(C_{1-6})$alkoxy$(C_{1-3})$alkyl group; a $(C_{1-6})$alkoxy$(C_{1-3})$ alkoxy$(C_{1-3})$alkyl group; a $(C_{1-6})$ alkylthio group; a halo$(C_{1-6})$alkylthio group; a $(C_{1-6})$ alkylsulfinyl group; a $(C_{1-6})$alkylsulfonyl group; a $(C_{1-6})$alkylthio$(C_{1-3})$alkyl group; a di$(C_{1-6})$alkoxy $(C_{1-3})$alkyl group in which the $(C_{1-6})$alkoxy groups may be the same or different; an unsubstituted amino $(C_{1-6})$alkyl group; a substituted amino $(C_{1-6})$alkyl group having one or two substituents which may be the same or different and are selected from the group consisting of $(C_{1-6})$alkyl groups, halo $(C_{1-6})$alkyl groups, $(C_{2-6})$alkenyl groups and $(C_{2-6})$ alkynyl groups; a cyano$(C_{1-6})$alkyl group; a $(C_{1-6})$ alkylcarbonyl group; a $(C_{1-6})$alkoxycarbonyl group; a hydroxycarbonyl$(C_{1-3})$alkyl group; a $(C_{1-6})$ alkoxycarbonyl$(C_{1-3})$alkyl group; an unsubstituted aminocarbonyl group; a substituted aminocarbonyl group having one or two substituents which may be the same or different and are selected from the group consisting of $(C_{1-6})$alkyl groups, $(C_{2-6})$alkenyl groups and $(C_{2-6})$alkynyl groups; a cycloalkyl$(C_{1-6})$alkyl group; an unsubstituted phenyl$(C_{1-3})$alkyl group; a substituted phenyl$(C_{1-3})$alkyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo $(C_{1-6})$alkoxy groups, $(C_{1-6})$alkylthio groups and halo $(C_{1-6})$alkylthio groups; an unsubstituted phenylcarbonyl group; a substituted phenylcarbonyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenylthio group; a substituted phenylthio group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenylsulfonyl group; a substituted phenylsulfonyl group having on the ring 1 to 5 substituents which may be the same or different and are selected from the group consisting of halogen atoms, nitro group, cyano group, $(C_{1-6})$alkyl groups, halo $(C_{1-6})$alkyl groups, $(C_{1-6})$alkoxy groups, halo$(C_{1-6})$alkoxy groups, $(C_{1-6})$alkylthio groups and halo $(C_{1-6})$alkylthio groups; an unsubstituted phenyl $(C_{1-6})$alkylsulfonyl group; a substituted phenyl$(C_{1-6})$ alkylsulfonyl group having on the ring 1 to 5 substituents which may be the same or different and are selected from the group consisting of halogen atoms, nitro group, cyano group, $(C_{1-6})$alkyl groups, halo $(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyloxycarbonyl group; a substituted phenyloxycarbonyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyloxy $(C_{1-3})$alkyl group; a substituted phenyloxy$(C_{1-3})$alkyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyl$(C_{2-6})$alkenyl group; a substituted phenyl$(C_{2-6})$alkenyl group having on the ring 1 to 5 substituents which may be the same or different and are selected from the group consisting of halogen atoms, nitro group, cyano group, $(C_{1-6})$alkyl groups, halo $(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups and $(C_{1-2})$ alkylenedioxy groups; a phenyl$(C_{2-6})$alkynyl group; a substituted phenyl$(C_{2-4})$alkynyl$(C_{1-3})$alkyl group having on the ring 1 to 5 substituents which may be the same or different and are selected from the group consisting of halogen atoms, nitro group, cyano group, $(C_{1-6})$alkyl groups, halo $(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups and $(C_{1-2})$alkylenedioxy groups; a 1,3-dioxolan-2-yl $(C_{1-3})$alkyl group; or a phthalimido $(C_{1-6})$alkyl group, $R^1$ is a 5- or 6-membered heterocyclic ring having 1 to 3 heteroatoms which may be the same or different and are selected from the group consisting of oxygen atom, sulfur atom and nitrogen atom, said heterocyclic ring having 1 to 5 substituents which may be the same or different and are selected from the group consisting of halogen atoms, cyano group, $(C_{1-6})$alkyl groups, halo $(C_{1-6})$alkyl groups and $(C_{1-6})$alkoxy groups, and the nitrogen atom in the heterocyclic ring being able to form an N-oxide group, Y is an oxygen atom or a sulfur atom, Z is —N=C (R²)—

(wherein $R^2$ is a hydrogen atom, a $(C_{1-6})$alkyl group or a halo $(C_{1-6})$alkyl group),

—N(R³)—CH(R²)—

(wherein $R^3$ is a hydrogen atom, a $(C_{1-6})$alkyl group, a formyl group, a $(C_{1-3})$alkylcarbonyl group, a halo$(C_{1-3})$alkylcarbonyl group or a $(C_{1-3})$alkyldithiocarbonyl group), or

—N(R³)—CO—

X's, which may be the same or different, are halogen atoms; hydroxyl groups; nitro groups; cyano groups; $(C_{1-6})$alkyl groups; halo$(C_{1-6})$alkyl groups; $(C_{1-6})$ alkoxy groups; halo$(C_{1-6})$alkoxy groups; $(C_{1-3})$ alkylenedioxy groups; hydroxycarbonyl groups; $(C_{1-6})$ alkoxycarbonyl groups; $(C_{2-6})$alkenyloxycarbonyl groups; $(C_{2-6})$alkynyloxycarbonyl groups; unsubstituted aminocarbonyl groups; substituted aminocarbonyl groups having one or two substituents which may be the same or different and are selected from the group consisting of $(C_{1-6})$alkyl groups, $(C_{2-6})$alkenyl groups and $(C_{2-6})$alkynyl groups; unsubstituted amino groups; or substituted amino groups having one or two substituents which may be the same or different and are selected from the group consisting of $(C_{1-6})$alkyl groups, $(C_{2-6})$alkenyl groups and $(C_{2-6})$alkynyl groups, and n is an integer of 0 or 1 to 4.

2. A substituted aminoquinazolinone (thione) derivative or a salt thereof according to claim 1, wherein R is a hydrogen atom; a formyl group; a $(C_{1-12})$alkyl group; a halo$(C_{1-6})$alkyl group; a $(C_{2-6})$alkenyl group; a $(C_{2-6})$ alkynyl group; a $(C_{1-6})$alkoxy group; a halo$(C_{1-6})$alkoxy group; a $(C_{1-6})$alkoxy$(C_{1-3})$alkyl group; a $(C_{1-6})$alkoxy $(C_{1-3})$alkoxy$(C_{1-3})$alkyl group; a $(C_{1-6})$alkylthio group; a halo$(C_{1-6})$alkylthio group; an unsubstituted amino$(C_{1-6})$ alkyl group; a substituted amino$(C_{1-6})$alkyl group having one or two substituents which may be the same or different and are selected from the group consisting of $(C_{1-6})$alkyl groups, halo$(C_{1-6})$alkyl groups, $(C_{2-6})$alkenyl groups and $(C_{2-6})$alkynyl groups; a cyano$(C_{1-6})$alkyl group; a $(C_{1-6})$ alkylcarbonyl group; a $(C_{1-6})$alkoxycarbonyl group; a hydroxycarbonyl$(C_{1-3})$alkyl group; a $(C_{1-6})$alkoxycarbonyl $(C_{1-3})$alkyl group; a $(C_{3-6})$cycloalkyl$(C_{1-3})$alkyl group; an unsubstituted phenyl$(C_{1-3})$alkyl group; a substituted phenyl $(C_{1-3})$alkyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$ alkoxy groups, halo$(C_{1-6})$alkoxy groups, $(C_{1-6})$alkylthio groups and halo$(C_{1-6})$alkylthio groups; an unsubstituted phenylcarbonyl group; a substituted phenylcarbonyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$ alkoxy groups, $(C_{1-6})$alkylthio groups and halo$(C_{1-6})$ alkylthio groups; an unsubstituted phenylthio group; a substituted phenylthio group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted pheny$(C_{2-6})$alkenyl group; a substituted phenyl $(C_{2-6})$alkenyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$ alkoxy groups, halo$(C_{1-6})$alkoxy groups, $(C_{1-6})$alkylthio groups, halo$(C_{1-6})$alkylthio groups and $(C_{1-2})$alkylenedioxy groups; a phenyl$(C_{2-6})$alkynyl group; or a substituted phenyl $(C_{2-4})$alkynyl$(C_{1-3})$alkyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups and $(C_{1-2})$alkylenedioxy groups, $R^1$ is a 5- or 6-membered heterocyclic ring having 1 to 3 heteroatoms which may be the same or different and are selected from the group consisting of oxygen atom, sulfur atom and nitrogen atom, said heterocyclic ring being able to have 1 to 5 substituents which may be the same or different and are selected from the group consisting of halogen atoms, cyano group, $(C_{1-6})$alkyl groups, halo$(C_{1-6})$alkyl groups and $(C_{1-6})$alkoxy groups, and the nitrogen atom in the heterocyclic ring being able to form an N-oxide group, Y is an oxygen atom or a sulfur atom, Z is

—N(R³)—CH(R²)—

(wherein R² is a hydrogen atom or a $(C_{1-6})$alkyl group, and R³ is a hydrogen atom, a $(C_{1-6})$alkyl group, a formyl group, a $(C_{1-3})$alkylcarbonyl group, a halo$(C_{1-3})$alkylcarbonyl group or a $(C_{1-3})$alkyldithiocarbonyl group), X's, which may be the same or different, are halogen atoms; hydroxyl groups; nitro groups; cyano groups; $(C_{1-6})$alkyl groups; halo$(C_{1-6})$alkyl groups; $(C_{1-6})$alkoxy groups; halo$(C_{1-6})$alkoxy groups; $(C_{1-3})$alkylenedioxy groups; hydroxycarbonyl groups; $(C_{1-6})$alkoxycarbonyl groups; $(C_{2-6})$alkenyloxycarbonyl groups; $(C_{2-6})$alkynyloxycarbonyl groups; unsubstituted aminocarbonyl groups; substituted aminocarbonyl groups having one or two substituents which may be the same or different and are selected from the group consisting of $(C_{1-6})$alkyl groups, $(C_{2-6})$alkenyl groups and $(C_{2-6})$alkynyl groups; unsubstituted amino groups; or substituted amino groups having one or two substituents which may be the same or different and are selected from the group consisting of $(C_{1-6})$alkyl groups, $(C_{2-6})$alkenyl groups and $(C_{2-6})$alkynyl groups, and n is an integer of 0 or 1 to 4.

3. A substituted aminoquinazolinone (thione) derivative or a salt thereof according to claim 2, wherein R is a hydrogen atom; a formyl group; a $(C_{1-12})$alkyl group; a halo$(C_{1-6})$alkyl group; a $(C_{2-6})$alkenyl group; a $(C_{2-6})$alkynyl group; a $(C_{1-6})$alkylthio group; a halo$(C_{1-6})$alkylthio group; a $(C_{1-6})$alkylcarbonyl group; a $(C_{1-6})$alkoxycarbonyl group; a $(C_{1-6})$alkoxycarbonyl$(C_{1-3})$alkyl group; an unsubstituted phenylcarbonyl group; a substituted phenylcarbonyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted pheny$(C_{2-6})$alkenyl group; a substituted phenyl$(C_{2-6})$alkenyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups and $(C_{1-2})$alkylenedioxy groups; a phenyl$(C_{2-6})$alkynyl group; or a substituted phenyl$(C_{2-4})$alkynyl$(C_{1-3})$alkyl group having on the ring 1 to 5 substituents which may be the same or different and are selected from the group consisting of halogen atoms, nitro group, cyano group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups and $(C_{1-2})$alkylenedioxy groups, R¹ is a pyridyl group, Y is an oxygen atom or a sulfur atom, Z is

—(R³)—CH(R²)—

(wherein R² is a hydrogen atom or a $(C_{1-6})$alkyl group, and R³ is a hydrogen atom or a $(C_{1-6})$alkyl group), X's, which may be the same or different, are halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-3})$alkylenedioxy groups, or $(C_{1-6})$alkoxycarbonyl groups, and n is an integer of 0 or 1 to 4.

4. A compound represented by the general formula (II):

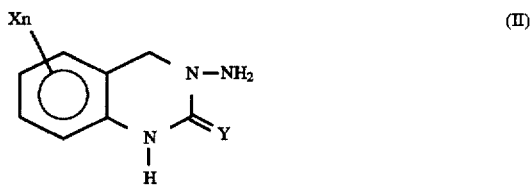

wherein X's, which may be the same or different, are halogen atoms; hydroxyl groups; nitro groups; cyano groups; $(C_{1-6})$alkyl groups; halo$(C_{1-6})$alkyl groups; $(C_{1-6})$alkoxy groups; halo$(C_{1-6})$alkoxy groups; $(C_{1-3})$-alkylenedioxy groups; hydroxycarbonyl groups; $(C_{1-6})$alkoxycarbonyl groups; $(C_{2-6})$alkenyloxycarbonyl groups; $(C_{2-6})$alkynyloxycarbonyl groups; unsubstituted aminocarbonyl groups; substituted aminocarbonyl groups having one or two substituents which may be the same or different and are selected from the group consisting of $(C_{1-6})$alkyl groups, $(C_{2-6})$alkenyl groups and $(C_{2-6})$alkynyl groups; unsubstituted amino groups; substituted amino groups having one or two substituents which may be the same or different and are selected from the group consisting of $(C_{1-6})$alkyl groups, $(C_{2-6})$alkenyl groups and $(C_{2-6})$alkynyl groups, n is an integer of 0 or 1 to 4, and Y is an oxygen atom or a sulfur atom.

5. A (pest controller) composition for controlling pests comprising as an active ingredient a substituted aminoquinazolinone (thione) derivative or a salt thereof set forth in claim 1.

6. A method for controlling pests which comprises applying a pest controller comprising as an active ingredient a substituted aminoquinazolinone (thione) derivative or a salt thereof set forth in claim 1, in a dosage of 0.01 g to 5 kg (in terms of the active ingredient) per 10 ares for controlling pests.

* * * * *